(12) United States Patent
Shafer et al.

(10) Patent No.: US 7,875,623 B2
(45) Date of Patent: Jan. 25, 2011

(54) PROCESS FOR REDUCING CONTAMINATING MICHAEL ACCEPTOR LEVELS IN OXYCODONE AND OTHER COMPOSITIONS

(75) Inventors: Jules A. Shafer, Gwynedd Valley, PA (US); Vladislav V. Telyatnikov, Hatfield, PA (US); Hao Wang, Singapore (SG)

(73) Assignee: Controlled Chemicals, Inc., Colmar, PA (US)

( * ) Notice: Subject to any disclaimer, the term of this patent is extended or adjusted under 35 U.S.C. 154(b) by 994 days.

(21) Appl. No.: 11/603,956

(22) Filed: Nov. 22, 2006

(65) Prior Publication Data

US 2007/0149559 A1    Jun. 28, 2007

Related U.S. Application Data

(60) Provisional application No. 60/739,087, filed on Nov. 22, 2005.

(51) Int. Cl.
*A61K 31/485* (2006.01)
*C07D 489/08* (2006.01)

(52) U.S. Cl. .................................. 514/282; 546/45
(58) Field of Classification Search .................. 514/282; 546/45
See application file for complete search history.

(56) References Cited

U.S. PATENT DOCUMENTS

2005/0222188 A1    10/2005   Chapman et al.
2006/0173029 A1    8/2006    Chapman et al.

OTHER PUBLICATIONS

Brogle, et al., "Peak fronting in reversed-phase high-performance liquid chromatogrphy: a study of the chromatographic behavior of oxycodone hydrochloride," *Journal of Pharmaceutical and Biomedical Analysis*, vol. 19, pp. 669-678 (1999).

*Primary Examiner*—Charanjit S Aulakh
(74) *Attorney, Agent, or Firm*—Wolf, Greenfield & Sacks, P.C.

(57) ABSTRACT

The present invention relates to processes for removal of Michael acceptors from certain compositions wherein the composition is treated with a thiol-containing compound under conditions sufficient to remove Michael acceptors and the resulting thiol-Michael adducts. Certain embodiments of the present invention enable quantification and/or removal of Michael acceptors and/or Michael acceptor precursors.

25 Claims, 11 Drawing Sheets

PROCESS FOR REDUCING CONTAMINATING MICHAEL ACCEPTOR LEVELS IN OXYCODONE AND OTHER COMPOSITIONS

RELATED APPLICATIONS

This application claims priority to U.S. Provisional Patent Application Ser. No. 60/739,087, filed Nov. 22, 2005.

BACKGROUND OF THE INVENTION

The presence of Michael acceptors as contaminants in pharmaceutical agents, food or other compositions that might be internalized by living organisms is generally undesirable, since Michael acceptors can undergo cytotoxic reactions with nucleophilic cellular constituents. Of particular concern are potentially genotoxic reactions of Michael acceptors with nucleic acid nucleophiles (e.g. Chem. Res. Toxicol. 2004, 17, 827-838; Chem. Res. Toxicol. 1991, 4, 50-7; Environmental Health Perspectives 1990, 88, 99-106).

Interestingly, animals have defense systems for deactivating internalized or metabolically generated Michael acceptors. One such deactivating system involves reaction of Michael acceptors with the endogenous cellular nucleophile, reduced glutathione, to form glutathione adducts (for a review see Advances in Enzyme Regulation 1993, 33, 281-296). Recent studies (Bioorg. Med. Chem. 1999, 7, 2849-2855; Chem. Commun. 2005, 886-888) indicate that this reaction is reversible. Thus, the genotoxic and carcinogenic potential of Michael acceptors may reflect a failure of the Michael acceptor to undergo complete reaction with glutathione or reversal of thiol addition. Consequently, it is important to minimize the amount of Michael acceptor contaminants (or Michael acceptor precursors) that are present in drugs and other products meant for administration to living organisms.

A recently published patent application (20050222188A1) entitled, "Process for preparing oxycodone hydrochloride having less than 25 PPM 14-hydroxycodeinone" describes a method for removal of the Michael acceptor 14-hydroxycodeinone from the analgesic composition oxycodone that involves hydrogenating in acidic solution an oxycodone hydrochloride composition that contains contaminating 14-hydroxycodeinone.

Whereas techniques like those described in 20050222188A1 (and elsewhere) exist for removal and detection of Michael acceptor contaminants, improvements would increase the safety of drugs and other compositions consumed by living organisms.

SUMMARY OF THE INVENTION

Figure 1:
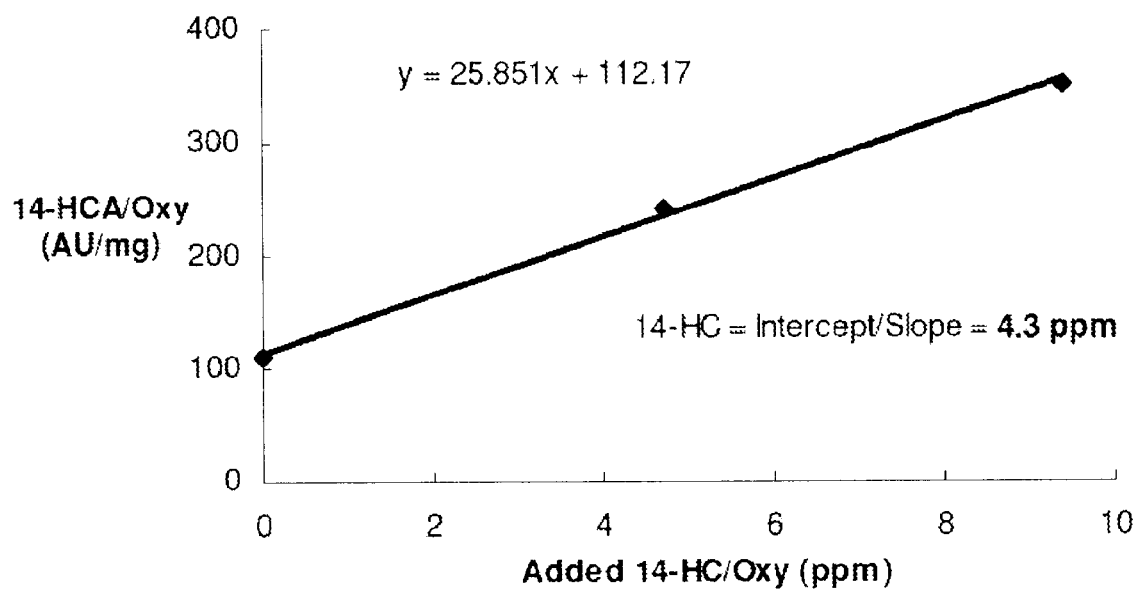
FIG. 1 depicts a plot used to determine the 14-hydroxycodeinone (14-HC) content of the oxycodone product of Example 1B with sodium thioglycolate.

The present invention, in one aspect, involves the processes as recited in the appended claims.

The present invention relates to processes for removal of Michael acceptors, and/or precursors thereof, from drugs or other compositions that contain ingredients that may be internalized by living organisms or compositions that might contact ingredients meant to be internalized by living organisms, wherein the composition is treated with a thiol-containing compound under conditions sufficient to remove Michael acceptors and thiol-Michael adducts. Where the text below refers to a process, it is to be understood that any of the processes described herein can apply.

In one aspect the invention provides a series of processes. One process involves removing at least one Michael acceptor from one or any combination of the following compositions: a composition that may be internalized by a living organism; a composition that may be in contact with a living organism; or a composition that may be in contact with materials suitable for internalization by a living organism; comprising treating the composition with a thiol-containing compound under conditions sufficient to remove at least a portion of the at least one Michael acceptor and/or a thiol-Michael adduct which can form from addition of the thiol-containing compound to the at least one Michael acceptor.

Another process of the invention involves removing at least one Michael acceptor from one or any combination of the following compositions: a composition that may be internalized by a living organism; a composition that may be in contact with a living organism; or a composition that may be in contact with materials suitable for internalization by a living organism; comprising treating the composition with a suitable soluble thiol-containing compound under conditions sufficient to react with the at least one Michael acceptor, and removing from the composition the resulting thiol-Michael adduct, and the unreacted thiol-containing compound, wherein the thiol-containing compound is chosen for its ability to form a soluble thiol-Michael adduct that can be removed from the composition of interest, and, when desirable, quantified, so as to enable determination of the Michael acceptor content of the composition of interest.

In processes of the invention, the composition of interest can be treated with a suitable thiol which has been immobilized on a solid support. The composition of interest can be selected from one or any combination of the following compositions: oxycodone; hydrocodone; oxymorphone; hydromorphone; naloxone; naltrexone or acceptable salt thereof; related alkaloid or acceptable salt thereof.

Processes of the invention can include producing a product, wherein no single Michael acceptor or salt thereof is present in an amount exceeding 5 ppm, or exceeding 10 or 25 ppm.

Product can be produced wherein no single thiol-Michael adduct or salt thereof is present in an amount exceeding 25 ppm. Product can be produced which contains oxycodone or acceptable salt thereof that contains 14-hydroxycodeinone or salt thereof in an amount of less than 25, less than 10, less than 5, or less than 1 ppm.

Product can be produced which contains oxycodone or acceptable salt thereof that contains 14-hydroxycodeinone or salt thereof in an amount of less than 1 ppm. Product can be produced which contains naltrexone or acceptable salt thereof that contains 7,8-dehydronaltrexone or salt thereof in an amount of less than 25, less than 10, less than 5, or less than 1 ppm.

Processes of the invention can also involve quantifying at least one Michael acceptor wherein the amount of thiol-Michael adduct is measured and related to the Michael acceptor content of the composition, and wherein the limit of quantification of the amount of any one Michael acceptor contaminant is 10 ppm or less, or wherein the limit of quantification of the amount of any one Michael acceptor contaminant is in the range of 0.001-10 ppm.

Processes of the invention can also involve quantifying the Michael acceptor content of one or any combination of the following compositions: oxycodone; hydrocodone; oxymorphone; hydromorphone; naloxone; naltrexone or acceptable salt thereof; or related alkaloid or acceptable salt thereof; wherein the amount of thiol-Michael adduct is measured and related to the Michael acceptor content of the composition, and wherein the limit of quantification of the amount of any one Michael acceptor contaminant is 10 ppm or less, or 1 ppm or less, or in the range of 0.001-10 ppm.

Processes of the invention can also involve quantifying the 14-hydroxycodeinone content of oxycodone or acceptable salt thereof wherein the amount of thiol-Michael adduct of 14-hydroxycodeinone is measured and related to the 14-hydroxycodeinone content of the composition, and wherein the limit of quantification of the level of the 14-hydroxycodeinone contaminant is 10 ppm or less, or less than 1 ppm, or within the range 0.001-10 ppm.

In processes of the invention, the composition of interest can be an organic base whose solubility in water decreases with increasing pH; and wherein the composition of interest is treated with a suitable thiol-containing compound in aqueous solution at a suitable pH value to form (with the contaminating Michael acceptor) a soluble thiol-Michael adduct; and wherein the organic base of interest is then separated from the thiol-Michael adduct and excess thiol-containing compound by raising the pH to a suitable value so as to precipitate the composition of interest from the solution of soluble thiol-Michael adduct and excess thiol-containing compound.

In processes of the invention, the composition of interest can be an organic acid whose solubility in water decreases with decreasing pH; and wherein the composition of interest is treated with a suitable thiol-containing compound in aqueous solution at a suitable pH value to form (with the contaminating Michael acceptor) a soluble thiol-Michael adduct; and wherein the organic acid of interest is then separated from the thiol-Michael adduct and excess thiol-containing compound by lowering the pH to a suitable value so as to precipitate the composition of interest from the solution of soluble thiol-Michael adduct and excess thiol-containing compound.

In processes of the invention, the composition of interest can be separated from thiol-Michael adduct and excess thiol-containing compound by selective precipitation and/or extraction utilizing water and/or other solvents and/or by selective absorption on media, such as, but not restricted to, ion-exchange resins, and/or other solid supports containing immobilized liganded metal ions, and/or immobilized maleimides, and/or immobilized reactive disulfides, and/or immobilized antibodies and/or immobilized enzymes.

Another process of the invention involves removing at least one Michael acceptor and/or at least one Michael acceptor hydrate from one or any combination of the following compositions: a composition that may be internalized by a living organism; a composition that may be in contact with a living organism; or a composition that may be in contact with materials suitable for internalization by a living organism; comprising treating the composition with an acid catalyst under conditions sufficient to remove at least one Michael acceptor hydrate by converting that one Michael acceptor hydrate to a Michael acceptor; and then treating the composition with a suitable soluble thiol-containing compound under conditions sufficient to remove from the composition the unreacted thiol-containing compound, at least one Michael acceptor originally present in the composition; and the Michael acceptor formed from the at least one Michael hydrate; and wherein the thiol-containing compound is chosen for its ability to form a soluble thiol-Michael adduct(s) that can be removed from the composition of interest, and, when desirable, quantified, so as to enable determination of the Michael acceptor hydrate content and the Michael acceptor content of the composition of interest. In this or other processes of the invention, the process can involve producing a product containing oxycodone or acceptable salt thereof that contains 8-hydroxyoxycodone or salt thereof in an amount of less than 100 ppm, or less than 10 ppm or less than 5 ppm. In this or other processes of the invention, the process can involve producing a product containing naltrexone or acceptable salt thereof that contains 8-hydroxynaltrexone or salt thereof in an amount of less than 100 ppm, or less than 10 ppm or less than 5 ppm.

The invention also provides a series of products, which can be produced according to processes described herein, or can be products which are essentially similar or identical to products which can be produced by processes of the invention. Any products which are described herein or would result from processes described herein are within the scope of the invention.

DETAILED DESCRIPTION OF THE INVENTION

The present invention relates to processes for removal of Michael acceptors, and precursors thereof, from drugs or other compositions that contain ingredients that may be internalized by living organisms or compositions that may contact ingredients meant to be internalized by living organisms, wherein the composition is treated with a thiol-containing compound under conditions sufficient to remove Michael acceptors and thiol-Michael adducts. Where the text below refers to a process, it is to be understood that any of the processes described herein can apply.

Definitions, as used herein:

"Michael acceptor" means an $\alpha,\beta$-unsaturated electrophile, such as, but not limited to, an $\alpha,\beta$-unsaturated carbonyl derivative or an $\alpha,\beta$-unsaturated nitrile.

It is to be understood that within the context of the definition of Michael acceptor: "Electrophile" means able to accept an electron pair; "$\alpha,\beta$-unsaturated electrophile" means the compound class that includes, but is not limited to, $\alpha,\beta$-unsaturated carbonyl derivative, $\alpha,\beta$-unsaturated nitrile, $\alpha,\beta$-unsaturated sulfone, or other vinyl derivative substituted with a strong electron withdrawing group, such as, but not limited to, a nitro group; "α,β-unsaturated carbonyl derivative" means the compound class that includes, but is not limited to, α,β-unsaturated ketone, quinone or derivative thereof, α,β-unsaturated aldehyde, α,β-unsaturated carboxylic acid derivative, such as, but not limited to, an ester, an amide, a substituted amide, or a maleimide or a derivative thereof.

"Thiol," or "thiol-containing compound," or "thiols" or "thiol-containing compounds" means thiol-containing compound, or compounds, except wherein the context of its use indicates a thiol moiety, or group, as in the term "thiol functionalized". Those of ordinary skill in the art are aware that a "thiol" is a sulfur-containing compound, generally a sulfur-containing organic compound.

"Thiol-Michael adduct" means a thioether, or mixture of thioethers, formed as a result of the addition of a thiol-containing compound to the Michael acceptor.

"Mercapto-thiol-Michael adduct" means a mercapto-thioether, or mixture of mercapto-thioethers, that form when a Michael acceptor reacts with an excess of a dithiol or polythiol (a compound containing at least two thiol groups).

"Michael acceptor precursor" means any substance (including a thiol-Michael adduct or Michael acceptor hydrate) that may undergo conversion to a Michael acceptor under conditions consistent with an environment in which the substance may exist in the context of the present invention. For example, a Michael acceptor precursor, in the context of a pharmaceutical or other therapeutic formulation, is a substance that can undergo conversion to a Michael acceptor as a result of conditions under which a pharmaceutical or therapeutic composition can exist during its synthesis, formation, storage, and/or use, whether prior to or after administration to a subject. A Michael acceptor hydrate is an example of a Michael acceptor precursor.

"Michael acceptor hydrate" means the product of addition of water to an α,β-unsaturated electrophile such as, but not limited to, a β-hydroxyketone.

"Processed composition" or "processed product" means a composition that has been subjected to a process of the present invention.

"HPLC" means high performance liquid chromatography.

"PPM" or "ppm" means parts per million by weight.

"Acceptable rate" means a rate consistent with the manufacturing cycle time needed to produce a competitively priced processed product.

"Suitable thiol," or, "Thiol suitable for Michael acceptor and/or precursor removal," means a thiol-containing compound that enables efficient removal of Michael acceptor and thiol-Michael adduct so as to enable production of a competitively priced processed product. Considerations and methods for selecting a suitable thiol-containing compound are described herein.

"Removing," "remove," "removed" or "removal," as used herein, pertains to reducing an amount, or reduction of an amount, of at least one Michael acceptor and/or corresponding thiol-Michael adduct, and/or thiol containing compound. In one set of embodiments, such species are removed by a factor of 5, 10, 20, 40, 60, 100, 500 or more. In another set of embodiments, removing involves removal of such species in an amount sufficient to detect the presence, concentration, and/or amount of such species in a composition.

"Separating," "separate," "separated" or "separation," as used herein, when pertaining to an operation, pertains to dividing up one or more compositions into two or more portions wherein certain components are enriched in one portion and others are enriched in other portions including situations where certain components are essentially completely depleted from at least one portion. For example, when components are separated by distribution between two phases (e.g. two immiscible liquids or a solid precipitate and liquid phase) the content of one or more components is enriched in one phase and depleted in the other. It is to be understood that compositions enriched in one phase may be also present in the other albeit at a lower level.

A "composition that may be internalized by a living organism" is a phrase that will be understood to those of ordinary skill in the art to include, but not be limited to, foods, pharmaceutical products, and the like.

A "composition that may be in contact with materials suitable for internalization by a living organism" is a phrase that would be understood by those of ordinary skill in the art to include, but not be limited to, pharmaceutical delivery equipment, food packaging, and other compositions and/or materials which are or/may be routinely in contact with compositions internalized by living organisms by preparation, storage, or use of such materials.

A "Michael acceptor, or electrophile, that can react with a nucleic acid" includes such species which can interact adversely with a nucleic acid, for example, species which can participate in potentially genotoxic reactions with nucleic acid nucleophiles.

Reaction of Michael acceptors with organic thiols to form thiol-Michael adducts is a well-documented reaction (Chem. Commun. 2005, 669-671 and work cited therein). The reaction has been shown to proceed in water and organic solvents. Both acidic and basic catalysts have been used to facilitate thiol-Michael adduct formation and minimize side reactions.

The documented reversibility of thiol-Michael adduct formation (Bioorg. Med. Chem. 1999, 7, 2849-2855; Chem. Commun. 2005, 886-888) suggests that removal of Michael acceptors from compositions using thiol reagents so as to produce products wherein the Michael acceptor level has been lowered by a factor of 20 or more will be problematical.

However, the teachings of this present invention, including the appended examples and claims, show how Michael acceptor levels can be reduced, in some embodiments, by over 20-fold to produce processed products with Michael acceptor levels below 10 ppm or other levels described herein; moreover, the teachings of the present invention, including the appended examples and claims, show how to quantify Michael acceptor levels with a limit of quantification at or below 10 ppm or other levels described herein.

Published literature (Bioorg. Med. Chem. 1999 7, 2849-2855; Chem. Commun. 2005, 886-888) indicates that in aqueous solution the rate of addition of a thiol to a Michael acceptor increases with increasing pH due to increased formation of thiolate anion. Thus, the invention appreciates that the observed pseudo first-order rate constant $k_R$ for formation of the thiol-Michael adduct (TM), should vary with the total concentration of thiol ($[T]_t = [TH]+[T^-]$), Michael acceptor concentration [M], and hydrogen ion concentration [H$^+$], according to the equation $$k_R = k_{s-}[T]_t/(1+[H^+]/K_{SH})$$

where $k_{s-}$ is the rate constant for reaction of the thiolate anion (T$^-$) with the Michael acceptor (M), and $K_{SH}$ is the acid dissociation constant for the thiol (TH).

It follows from the law of microscopic reversibility that the rate of elimination of thiolate anion from a thiol-Michael adduct is dependent on the fraction of thiol-Michael adduct existing as a carbanion. Thus, the overall reaction can be represented as proceeding via the following three-step reaction pathway.

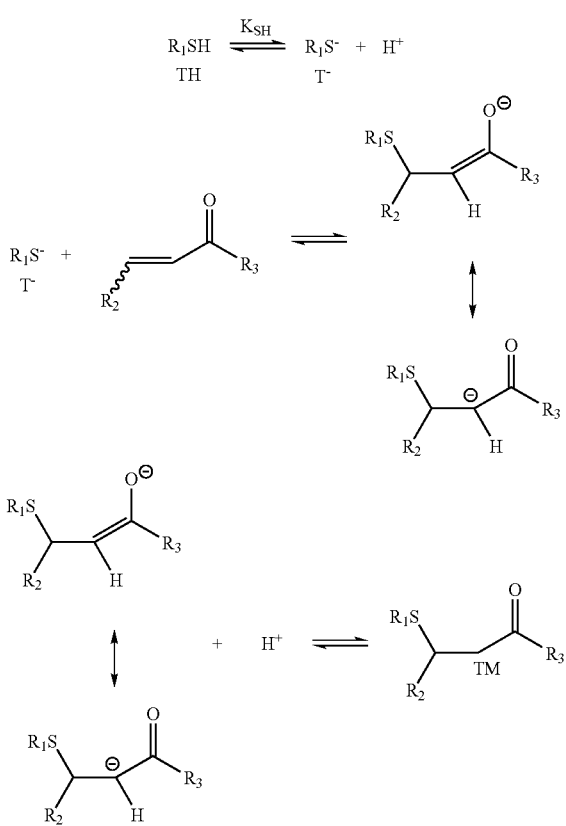

The first and third steps of the reaction pathway involve proton transfer reactions that appear to be diffusion controlled in the thermodynamically favored direction, whereas the rates of adduct formation and decomposition in the second step appear to be the rate determining steps for the overall reaction pathway. The rate and position of the equilibrium for addition of thiolate anion to the Michael acceptor will, of course, reflect the properties of the thiolate anion and the Michael acceptor. These considerations account for observations that the rate of equilibration of thiol, Michael acceptor, and thiol-Michael adduct increases with increasing pH. The observation (Bioorg. Med. Chem. 1999, 7, 2849-2855), that the extent of adduct formation at equilibrium decreases with increasing pH, however, has not been accounted for quantitatively.

From the equation for the overall reaction,

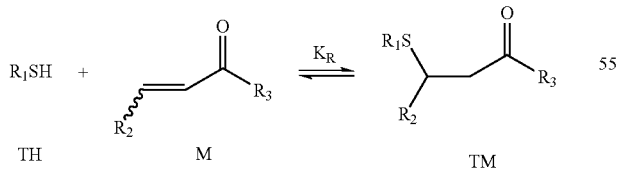

and the equilibrium expressions for the overall reaction and the ionization of the thiol group $$K_R=[TM]/[TH][M] \quad K_{SH}=[T^-][H]/[TH]$$

it follows that $$[TM]/[M]=K_R[T]_t/(1+K_{SH}/[H^+]).$$

This expression allows for the first time, as a contribution made by this invention, quantitative prediction of the dependence of the equilibrium concentration ratio of thiol-Michael adduct [TM] and Michael acceptor [M] on the hydrogen ion concentration. The latter expression together with the expression for $K_R$ described herein teaches how decreasing the hydrogen ion concentration decreases the extent of thiol-Michael adduct formation and increases the rate of adduct formation, and enables the design of the processes of the present invention for the removal of Michael acceptors from oxycodone and other compositions.

Oxycodone is a semisynthetic opiate produced via an oxidative conversion of the natural product thebaine to 14-hydroxycodeinone as depicted in the following scheme.

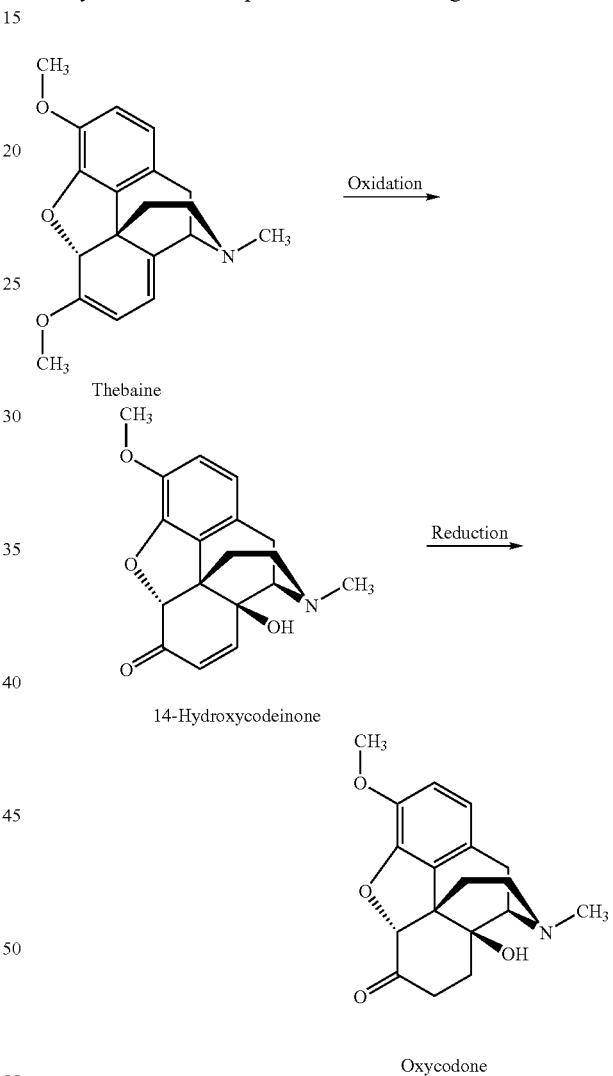

The oxycodone precursor 14-hydroxycodeinone is a Michael acceptor that commonly contaminates oxycodone preparations. The process of this invention for Michael acceptor removal is useful for removing 14-hydroxycodeinone from oxycodone. It involves treating oxycodone with a thiol so as to convert 14-hydroxycodeinone to a thiol-Michael adduct. In one embodiment of the invention the reaction is carried out in water at a suitable pH. The pH is chosen so as to allow one to obtain both a reasonably concentrated homogenous solution of oxycodone and a reasonable rate of reaction consistent with the production of a competitively priced oxycodone processed product. For formation of a thiol-Michael adduct in water in certain embodiments of this invention, a water soluble thiol is chosen so as to form a thiol-Michael adduct having properties that enable reduction of the Michael acceptor content to less than 10 ppm. In other embodiments Michael acceptor content is reduced to less than 2000, 1000, 500, 200, 100, 50, 25, 10, 5, 2, 1, 0.5, or 0.25 ppm in accordance with the invention. The invention also can reduce Michael acceptor levels by over 20-fold, for example at least 40-fold, 60-fold, 80-fold, 100-fold, 500-fold, 1,000-fold, or at least 2,000-fold. In one application of the invention to the purification of oxycodone, a 7.5% oxycodone solution is treated at pH 6 with 20 mM sodium thioglycolate and 2 mM EDTA (added to suppress trace metal ion catalyzed thiol oxidation) for 2.8 hours at room temperature.

The knowledge that oxycodone solubility increases with increases in the hydrogen ion concentration [H$^+$] according to the following relationship, Total concentration of dissolved oxycodone=[Oxy]$_s$+ [OxyH$^+$]=[Oxy]$_s$(1+[H$^+$]/K), where [Oxy]$_s$ is the solubility of oxycodone free base, and K is the acid dissociation constant for the conjugate acid of oxycodone (OxyH$^+$), the relationship between k$_R$, the thiol concentration, and hydrogen ion concentration disclosed above, and the understanding that the rate of reaction increases with temperature, in conjunction with the disclosures herein, enables one skilled in the art to efficiently identify other desirable reaction conditions. For example, one could carry out a homogenous reaction at a substantially higher oxycodone concentration by lowering the pH to increase the obtainable amount of dissolved oxycodone. To compensate for the lowered reaction rate at lower pH, one skilled in the art, guided by factors described herein can, if necessary, suitably increase the concentration of thiol, and/or the temperature, and/or the reaction time.

Well-established analytical methods, such as those utilizing high performance liquid chromatography or gas chromatography linked to systems that monitor a property of the effluent stream such as absorbance, fluorescence, light scattering, conductance, refractive index or mass spectrum, can be employed by one skilled in the art to quantify the build-up of thiol-Michael adduct in acid quenched reaction mixtures, and thereby characterize the time dependence of the conversion of Michael acceptor to thiol-Michael adduct as a function of thiol structure, thiol concentration, reaction medium, and temperature. For example, if one reacts a Michael acceptor in the presence of a greater than ten-fold molar excess of thiol while keeping the fraction of thiol present as thiolate anion constant (in water, by maintaining a constant pH during the reaction by addition of acid or base, or by addition of a suitable buffer; in an organic solvent, by the addition of an organic acid or base or mixtures thereof), one skilled in the art can determine a pseudo first-order rate constant for the formation of thiol-Michael adduct. Since this pseudo first-order rate constant is proportional to the thiolate anion concentration as described herein, as well as a function of the structure of the thiol and temperature, measurements of the pseudo first-order rate constant for a small number of reactions enables one to efficiently select a suitable thiol, a suitable thiol concentration, a suitable pH (for reactions in water) or base (for reactions in an organic solvent), a suitable time, and a suitable temperature for obtaining an acceptable extent of conversion to thiol-Michael adduct. A reaction mixture, comprised of 20 mM thiol with 0.1-10% of the thiol present as thiolate anion (obtained by appropriate adjustment of pH (for reactions in water) or by addition of an appropriate base (for reactions in an organic solvent)), and <2 mM Michael acceptor in the presence or absence of the composition of interest, is usually a suitable starting point for a screen to identify optimal reaction conditions.

Subsequent to thiol-Michael adduct formation, the composition of interest can be removed from thiol-Michael adduct and/or excess thiol in certain embodiments of this invention. This removal can be in large amount, for example for modification of a composition to render it suitable for human consumption or other clinical use, or removal can be in a different amount (e.g., smaller amount) for detection/determination of the presence and/or quantity of a Michael acceptor in a composition. Suitable thiols for use in the reaction include, but are not limited to, those described herein including those noted in the appended claims. As discussed in the following paragraphs, and illustrated in the examples and the appended claims, the suitability of the thiol is dependent on the composition of interest and the context of the use of the thiol.

Suitable thiols are ones that can be efficiently removed from the composition of interest and form thiol-Michael adducts that can be efficiently removed from the composition of interest, and form thiol-Michael adducts that undergo little or no conversion back to Michael acceptor under conditions used to remove the thiol-Michael adduct from the composition of interest, and undergo no substantial conversion back to Michael acceptor after internalization (in cases where the thiol-Michael adduct is not adequately removed from the composition of interest). In cases where the thiol-Michael adduct is retained in the processed composition, it is necessary to demonstrate that, during the shelf life of the processed composition, the amount of thiol-Michael adduct formed from the thiol-Michael adduct retained in the processed composition is not a cause for concern by individuals and agencies competent to oversee the safety of food or drugs or medical devices.

The stability of a thiol-Michael adduct in a particular medium (e.g., the media being considered for separation of the composition of interest from the thiol-Michael adduct, or physiological fluids that the thiol-Michael adduct is likely to contact after internalization) or during storage can be evaluated from measurements of the time-dependent decrease in thiol-Michael adduct concentration.

In certain embodiments of the present invention, processed products are produced with a Michael acceptor level that is less than 100, 10, 5, 2, 1, 0.5, 0.1 or 0.01 ppm and a thiol-Michael adduct level that is less than 500, 100, 10, 5, 2, 1, 0.5, 0.1, or 0.01 ppm.

Embodiments of the present invention include processes wherein soluble thiol-containing compounds are chosen so as to form soluble thiol-Michael adducts that can be effectively removed from a composition of interest, and facilitate quantification of low levels of Michael acceptor contaminants in a composition that would otherwise be difficult to measure directly due to interference from the composition of interest. Thus, in certain embodiments of the present invention, the Michael acceptor content of a composition is determined by treating the composition with a suitable thiol-containing compound, removing the thiol-Michael adduct from the composition of interest and/or thiol-containing compound to enable quantification of the thiol-Michael adduct, and relating the amount of thiol-Michael adduct to the Michael acceptor in the composition of interest. Well-established analytical methods, such as those utilizing high performance liquid chromatography or gas chromatography linked to systems that monitor a property of the effluent stream such as absorbance, fluorescence, light scattering, conductance, refractive index or mass spectrum of the effluent stream, can be used by one skilled in the art to quantify thiol-Michael adducts. Thus, certain embodiments of the present invention quantify Michael acceptor levels in processed and unprocessed compositions of interest with a limit of quantification that is less than 100, 10, 5, 1, 0.1 and 0.01 ppm.

In embodiments of the present invention wherein subsequent to thiol adduct formation the thiol-Michael adduct, and/or excess thiol is removed from the composition of interest, the thiol is chosen so as to endow the thiol-Michael adduct with properties that differ from those of the composition of interest. These properties include, but are not restricted to, a different solubility in an organic solvent or water/organic solvent mixtures, or in water at a suitable pH value, and/or a different affinity for an ion-exchange resin and/or another solid medium, such as one containing an immobilized disulfide-containing compound, an immobilized maleimide-containing compound, and/or a different affinity on an immobilized antibody or fragment thereof, or an immobilized enzyme or fragment thereof.

The following considerations nicely illustrate how the teachings of the present invention guide the choice of a suitable thiol-containing compound. Subsequent to formation of thiol-Michael adduct at pH~6 in one embodiment of the process used to remove 14-hydroxycodeinone from oxycodone, the pH of the reaction mixture is increased to precipitate and/or extract oxycodone free base from an aqueous solution with most of the thiol-Michael adduct and excess sodium thioglyclolate remaining in aqueous solution. The already mentioned expression for the pH-dependence of oxycodone solubility in water indicates the desirability of a basic pH for efficient precipitation and/or extraction of oxycodone free base. The relationship $[TM]/[M]=K_R[T]_r/(1+K_{SH}/[H^+])$ disclosed in the teachings of the present invention indicates that raising the pH to 9 will result in little conversion of the thiol-Michael adduct (formed at pH~6 where oxycodone is soluble) back to 14-hydroxycodeinone when sodium thioglycolate ($pK_{SH}$ 10.3) is used. With a thiol with a $pK_{SH}$ of 10.3, raising the pH from 6 to 9 would result in only a 5% decrease in the equilibrium ratio $[TM]/[M]$. Thus, under conditions wherein thiol-adduct formation is highly favored at pH 6 for at specified thiol concentration, raising the pH from 6 to 9 would only increase the Michael acceptor content by 5%. Using a pK 9 thiol, however, would lead to a two-fold decrease in the equilibrium ratio $[TM]/[M]$ when the pH is increased from 6 to 9. Lowering the pH used for precipitating or extracting the oxycodone would, of course, decrease the extent of the back reaction but would also make it more difficult to recover oxycodone product because lowering the pH increases the aqueous solubility of oxycodone. Examples included in the present invention illustrate processes that use a lower pH for precipitation and/or extraction of oxycodone and/or processes that use lower pK thiols. It is interesting to note that although 5-mercapto-2-nitro-benzoic acid (pK 4.8) is not readily compatible with a process involving precipitation and/or extraction of oxycodone from a basic solution containing the thiol-Michael adduct formed from 5-mercapto-2-nitro-benzoic acid, this thiol-containing compound can be employed for processes (especially processes that involve quantification of a Michael acceptor contaminant in a composition) that utilize other methods to remove Michael acceptor from thiol-Michael adduct and unreacted thiol.

Thus, in certain embodiments of the present invention subsequent to treatment with the thiol-containing compound, the composition of interest is substantially removed from thiol-Michael adduct and excess thiol-containing compound by, but not restricted to, one or any combination of the following operations: selective precipitation from an aqueous solution induced by adjustment of the pH of the solution; selective extraction into a water immiscible solvent from an aqueous solution with, when appropriate, adjustment of the pH (to facilitate extraction), the thiol-content (to suppress thiol-Michael adduct decomposition), and the salt content (to facilitate phase separation) of the aqueous solution; selective precipitation from an aqueous solution by addition of one or more water miscible organic solvents; selective extraction from a water immiscible organic solvent into an aqueous solution at an appropriate pH, and thiol-content; selective precipitation from a water miscible organic solvent by addition of an aqueous solution; selective precipitation from an organic solvent or a mixture of organic solvents by addition of a second organic solvent or mixture of organic solvents; high performance liquid chromatography; or selective absorption on, or reaction with, a solid medium comprised of, but not limited to, any one or any combination of the following solid media: ion-exchange resin; a solid medium functionalized with a maleimide moiety; a solid medium functionalized with a reactive disulfide; a solid medium functionalized with a chelated metal ion; or a solid medium containing an immobilized protein.

In other embodiments of the invention, a thiol-containing compound, such as, but not restricted to, thioglycolic acid, 2-mercaptoethanesulfonic acid, glutathione, cysteine, homocysteine, mercaptosuccinic acid, thioglycerol, 2-aminoethanethiol, a dithiol such as, but not restricted to, ethanedithiol, dithiothreitol, reduced lipoic acid (where it is desirable to form a mercapto-thiol-Michael adduct), or thiol-containing compound immobilized on a solid support, is used (depending on the properties of the composition of interest and the Michael acceptor) to form a thiol-Michael adduct that can be efficiently removed from the composition of interest. Solid supports containing an immobilized thiol are commonly used to sequester heavy metal ions and are commercially available. Thiol functionalized solid media also can be obtained by reaction of a solid support containing an immobilized N-hydroxysuccinimide ester or p-nitrophenyl ester or other amine reactive ester with an aminothiol, such as, but not limited to, glutathione, 2-aminoethanethiol, or cysteine, or by reacting solid medium functionalized with an organic halide or a maleimide with a dithiol, such as, but not limited to, ethanedithiol, or reduced lipoic acid.

It is important to note that selection of the most suitable thiol for a process may require a detailed cost analysis of the process that takes into account the observations that certain soluble thiol-containing compounds may allow shorter manufacturing cycle times, may be less costly, and may enable facile determination of Michael acceptor levels, whereas certain thiol functionalized solid media may provide more convenient removal of the thiol-Michael adduct.

Certain embodiments of the present invention involve removal of a Michael acceptor from a composition comprised of an organic base, such as oxycodone, whose solubility in water decreases with increasing pH. Such embodiments may involve treatment of the composition of interest with a suitable soluble thiol-containing compound such as, but not restricted to, sodium thioglycolate, cysteine hydrochloride, sodium 2-mercaptoethanesulfonate, 5-mercapto-2-nitro-benzoic acid, or N-dansylcysteine, and formation (in aqueous solution at a suitable pH) of a soluble thiol-Michael adduct. The organic base of interest may be precipitated from the solution of soluble thiol-Michael adduct and excess thiol-containing compound by raising the pH to a suitable value. Further unit operations may be required to remove co-precipitated thiol-Michael adduct from the precipitated composition.

Other embodiments of the present invention involve removal of a Michael acceptor from a composition, such as an organic acid, whose solubility in water decreases with decreasing pH. Such embodiments may involve treatment of the composition of interest with a suitable soluble thiol-containing compound, such as, but not restricted to, cysteine hydrochloride, sodium 2-mercaptoethanesulfonate, or 2-aminoethanethiol, and formation (in aqueous solution at a suitable pH) of a soluble thiol-Michael adduct. The organic composition of interest may be precipitated from the solution of soluble thiol-Michael adduct and excess thiol-containing compound by lowering the pH to a suitable value. Further unit operations may be required to remove co-precipitated thiol-Michael adduct from the precipitated composition.

Other embodiments of the present invention may involve removal of contaminating Michael acceptor wherein it is desirable to carry out the reaction in a non-aqueous solvent because the composition of interest has a poor solubility in water.

Such cases may involve treatment of the composition of interest with a suitable thiol such that the thiol and/or thiol-Michael adduct can be removed from the composition of interest. A thiol, such as, but not limited to, 2-aminoethanethiol, could be a suitable thiol for these embodiments of the present invention since 2-aminoethanethiol could form a thiol-Michael adduct that could be extracted into aqueous acid and, thereby, removed from a water insoluble composition of interest. Further unit operations may be required to remove co-precipitated thiol-Michael adduct from the precipitated composition of interest.

Still other embodiments of the present invention include the detection and removal of a Michael acceptor hydrate. Removal of this Michael acceptor precursor from a composition may be desirable in cases wherein its conversion to a Michael acceptor is significant. Certain embodiments of the present invention include conversion of the Michael acceptor hydrate to a Michael acceptor by treatment with an acidic catalyst and subsequent removal and/or quantification of the Michael acceptor via its conversion to a thiol-Michael adduct using the teachings of the present invention.

The appended examples illustrate application of processes of the present invention for reducing Michael acceptor levels in oxycodone and related compositions and/or quantifying Michael acceptor levels in oxycodone and related compositions.

The appended examples, together with the other teachings herein, including the appended claims, enable one skilled in the art to apply embodiments of the present invention to cases not specifically illustrated by an example. These additional embodiments of the present invention include, but are not limited to, cases wherein:

The Michael acceptor and the composition of interest are chosen from, but not limited to, one or more of the following examples:

i. The Michael acceptor is acrylonitrile; and the composition of interest is produced via a process utilizing acrylonitrile, and is selected from, but not restricted to, one or more of the following compositions: styrene-acrylonitrile; and acrylonitrile-butadiene-styrene; and acrylonitrile-methyl methacrylate polymers.

ii. The Michael acceptor is acrylamide; and the composition of interest is produced via a process utilizing acrylamide, and is selected from, but not restricted to, one or more of the following compositions: polyacrylamide and copolymers thereof.

iii. The Michael acceptor is methyl acrylate; and the composition of interest is produced via a process utilizing methyl acrylate, and is selected from, but not restricted to, one or more of the following compositions: Vitamin B1; poly(methyl acrylate) and copolymers thereof.

iv. The Michael acceptor is ethyl acrylate; and the composition of interest is produced via a process utilizing ethyl acrylate, and is selected from, but not restricted to, one or more following compositions: poly(ethyl acrylate) and copolymers thereof.

v. The Michael acceptor is methyl methacrylate; and the composition of interest is produced via a process utilizing methyl methacrylate, and is selected from, but not restricted to, one or more of the following compositions: poly(methyl methacrylate) and copolymers thereof.

vi. The Michael acceptor is 2-ethylhexyl acrylate; and the composition of interest is produced via a process utilizing 2-ethyl acrylate, and is selected from, but not restricted to, one or more of the following compositions: poly(2-ethylhexyl acrylate) and copolymers thereof.

vii. The Michael acceptor is crotonaldehyde; and the composition of interest is produced via a process utilizing crotonaldehyde, and is selected from, but not restricted to, one or more of the following compositions: 2-ethylhexyl alcohol; butyraldehyde and quinaldine.

viii. The Michael acceptor is methyl vinyl ketone; and the composition of interest is produced via a process utilizing methyl vinyl ketone, and may be selected, but not restricted to, Vitamin A.

ix. The Michael acceptor is acrolein; and the composition of interest is cigarette, cigar, or pipe smoke.

Unless specified otherwise, all operations in the following examples were carried out at room temperature.

EXAMPLE 1A

Removal of 14-hydroxycodeinone from an Oxycodone Composition

This example describes treatment of an oxycodone free base composition containing more than 300 ppm but less than 1000 ppm of 14-hydroxycodeinone with 20 mM sodium thioglycolate at pH 6 to effect (together with other operations) removal of 14-hydroxycodeinone and the thiol-Michael adduct, and produce a processed product containing less than 10 ppm of 14-hydroxycodeinone.

An oxycodone sample containing more than 300 ppm of 14-hydroxycodeinone was dissolved in water at pH 6.0 to produce a 7.5% solution (75 mg/mL) using 4 M HCl to effect neutralization and dissolution of the oxycodone to pH 6. Sufficient solid EDTA and solid sodium thioglycolate were added to bring the concentrations of these components in the reaction mixture to 2 mM EDTA and 20 mM thioglycolate. The pH was maintained at pH 6.0, at room temperature for 2.8 hours, after which time the reaction mixture was raised to pH 9 to precipitate the oxycodone from the solution containing the thioglycolate-Michael adduct, and excess thioglycolate. The precipitated oxycodone was washed with pH 9, 0.05 M sodium bicarbonate buffer, and dissolved in ethyl acetate. The ethyl acetate solution of oxycodone was extracted with pH 9.0, 0.05 M sodium bicarbonate buffer, and the ethyl acetate removed under reduced pressure to yield oxycodone containing less than 10 ppm of 14-hydroxycodeinone.

EXAMPLE 1B

Removal of 14-hydroxycodeinone from an Oxycodone Composition with 20 mM Sodium Thioglycolate This example describes treatment of an oxycodone free base composition containing 3525 ppm of 14-hydroxycodeinone with 20 mM sodium thioglycolate to effect (together with other operations) a more than 800-fold reduction in 14-hydroxycodeinone content of the composition and produce a product wherein the sum of the 14-hydroxycodeinone and the 2-(oxycodone-8-sulfanyl)-acetic acid content was less than 5 ppm.

Oxycodone (5.0 g, 15.9 mmol) containing 3525 ppm of 14-hydroxycodeinone was dissolved in 50 mL of 0.33 N HCl. The pH of the resulting solution was raised to 6.1-6.2 by addition of 1 M sodium carbonate with stirring. After dissolution of any oxycodone that precipitated during the addition of the sodium carbonate, sodium thioglycolate, chosen as a thiol-containing compound (0.114 g, 1 mmol) was added. The resulting solution was stirred for 1 h and then solid sodium carbonate (1.5 g, 14.2 mmol) was added to the solution with vigorous stirring. After ~6 min (the pH of the solution increased to approximately 7.6), the oxycodone suspension was extracted into ethyl acetate (250 mL), and the ethyl acetate extract was vigorously stirred with 50 mL of aqueous 20 mM sodium thioglycolate for 20 min. After separation of the sodium thioglycolate wash, the ethyl acetate solution of oxycodone was washed with 50 mL of water and stirred with 50 mL of 0.33 N HCl for 30 min to extract the oxycodone into the aqueous acid. The aqueous layer was separated and the pH was raised to 9.1-9.3 with 1 M sodium carbonate (~22 mL) to precipitate oxycodone free base. The precipitate was collected, washed with 25 mL of water, and dried in a desiccator under reduced pressure to yield 4.7 g (94% yield) of an oxycodone product, wherein the sum of the 14-hydroxycodeinone and the 2-(oxycodone-8-sulfanyl)-acetic acid (thiol-Michael adduct) content was less than 5 ppm (see EXAMPLES 2-3).

EXAMPLE 2

Determination of the Sum of 14-hydroxycodeinone Content and the 2-(oxycodone-8-sulfanyl)-acetic Acid Content of the Oxycodone Product of Example 1B The oxycodone product of EXAMPLE 1B (0.5 g, 1.6 mmol) was dissolved in 0.2 N HCl (10 mL). Ethylenediaminetetraacetic acid (EDTA) (0.005 g, 0.017 mmol) was added and the solution pH was raised to 6.1-6.2 with 1 M sodium carbonate with stirring to dissolve any precipitated oxycodone. To the homogeneous reaction mixture was added sodium thioglycolate (0.025 g, 0.22 mmol). In separate spike experiments known amounts of 14-hydroxycodeinone were introduced prior to addition of sodium thioglycolate. After 1.5 h, the pH of the solution was raised to 8.2-8.4 with 1 M sodium carbonate (~1.6 mL) and the suspension was extracted with dichloromethane (2×15 mL) in a 30 mL separatory funnel. The aqueous layer was separated and acidified with 1 N HCl (1.7 mL) to pH 2.6-3.6. An aliquot (2 mL) of the predetermined volume of the aqueous -solution (15-16 mL) was evaporated to dryness under reduced pressure on a rotary evaporator at 30-40° C. and the residue was dissolved in 0.07% trifluoroacetic acid/water (200 uL). An aliquot of the solution was analyzed by HPLC, wherein an analyte in the effluent stream was quantified from its absorbance at 280 nm. The sum of the 14-hydroxycodeinone content and 2-(oxycodone-8-sulfanyl)-acetic acid content was 4.3 ppm as calculated from a plot of the area under the 2-(oxycodone-8-sulfanyl)-acetic acid peak per milligram of oxycodone analyzed versus the amount of 14-hydroxycodeinone added (ppm, i.e. micrograms of 14-hydroxycodeinone added per gram of oxycodone) as shown in FIG. 1.

Plotted on the ordinate is the ratio of the area obtained for the peak corresponding to the thiol-Michael adduct 2-(oxycodone-8-sulfanyl)-acetic acid (14-HCA) and the weight of oxycodone (Oxy) analyzed (Area Units (AU)/mg). Plotted on the abscissa is the ratio of the weight of the 14-hydroxycodeinone (14-HC) spike and the weight of oxycodone analyzed (ppm).

EXAMPLE 3

Determination of the 2-(oxycodone-8-sulfanyl)-acetic Acid Content of the Oxycodone Product of Example 1B The oxycodone product of EXAMPLE 1B (0.51 g, 1.6 mmol) was dissolved in dichloromethane (3 mL) and the solution was extracted with water (3 mL). An aliquot (1 mL) of the aqueous extract was acidified with 1 N HCl (10 uL) and evaporated to dryness under reduced pressure on a rotary evaporator at 30-40° C. The residue was dissolved in 0.07% trifluoroacetic acid/water (200 uL) and an aliquot of the solution was analyzed by HPLC, wherein an analyte in the effluent stream was quantified from its absorbance at 280 nm. The content of 2-(oxycodone-8-sulfanyl)-acetic acid in the sample was equal to or less than 0.1 ppm.

EXAMPLE 4

Determination of the 14-hydroxycodeinone Content of the Oxycodone Product of Example 1B The 14-hydroxycodeinone content was determined by subtracting the 2-(oxycodone-8-sulfanyl)-acetic acid content of the oxycodone product as determined in EXAMPLE 3 from the sum of the 14-hydroxycodeinone content and the 2-(oxycodone-8-sulfanyl)-acetic acid content of the oxycodone product as determined in EXAMPLE 2. Thus, the 14-hydroxycodeinone content of the oxycodone product of EXAMPLE 1 was $\leq 4.3$ ppm.

EXAMPLE 5

Removal of 14-hydroxycodeinone from an Oxycodone Composition with 20 mM Sodium 2-mercaptoethanesulfonate This example describes treatment of an oxycodone free base composition containing 3525 ppm of 14-hydroxycodeinone with 20 mM sodium 2-mercaptoethanesulfonate to effect (together with other operations) a more than 300-fold reduction in 14-hydroxycodeinone content of the composition and produce a product wherein the sum of the 14-hydroxycodeinone and the 2-(oxycodone-8-sulfanyl)-ethanesulfonic acid content was less than 15 ppm.

Oxycodone (5.0 g, 15.9 mmol) containing 3525 ppm of 14-hydroxycodeinone was dissolved in 50 mL of 0.33 N HCl.

The pH of the resulting solution was raised to 6.1-6.2 by addition of 1 M sodium carbonate with stirring. After dissolution of any oxycodone that precipitated during the addition of the sodium carbonate, sodium 2-mercaptoethanesulfonate (0.165 g, 1 mmol) was added, the resulting solution stirred for 1 h and solid sodium carbonate (1.5 g, 14.2 mmol) then added to the solution with vigorous stirring. After ~6 min (the pH of the solution increased to approximately 7.6), the oxycodone suspension was extracted into ethyl acetate (250 mL), and the ethyl acetate extract was vigorously stirred with 50 mL of aqueous 20 mM sodium 2-mercaptoethanesulfonate solution for 20 min. After removal of the sodium 2-mercaptoethanesulfonate wash, the ethyl acetate solution of oxycodone was washed with 50 mL of water and stirred with 50 mL of 0.33 N HCl for 10 min to extract the oxycodone into the aqueous acid. The aqueous layer was separated and the pH was raised to 9.2-9.4 with 1 M sodium carbonate (~22 mL) to precipitate oxycodone free base. The precipitate was collected, washed with 25 mL of water, and dried in a desiccator under reduced pressure to yield 4.7 g (94% yield) of an oxycodone product; wherein the sum of the 14-hydroxycodeinone content and the 2-(oxycodone-8-sulfanyl)-ethanesulfonic acid content was less than 15 ppm (see EXAMPLES 6-7).

EXAMPLE 6

Determination of the 14-hydroxycodeinone Content of the Oxycodone Product of Example 5

Figure 2:
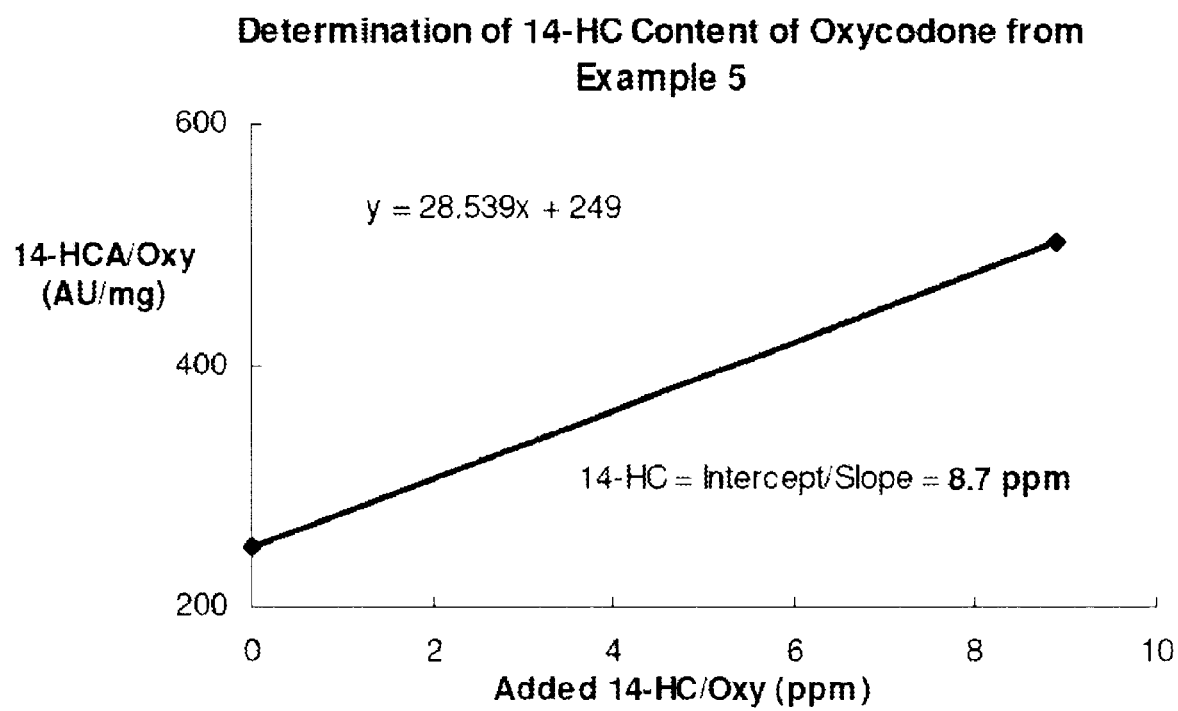
FIG. 2 depicts a plot used to determine the 14-hydroxycodeinone (14-HC) content of the oxycodone product of Example 5 with sodium thioglycolate.

The oxycodone product of EXAMPLE 5 (0.5 g, 1.6 mmol) was dissolved in 0.2 N HCl (10 mL). EDTA (0.005 g, 0.017 mmol) was added and the solution pH was raised to 6.1-6.2 with 1 M sodium carbonate with stirring to dissolve any precipitated oxycodone. To the homogeneous reaction mixture was added sodium thioglycolate (0.025 g, 0.22 mmol). In separate spike experiments known amounts of 14-hydroxycodeinone were introduced prior to addition of sodium thioglycolate. After 1.5 h the pH of the solution was raised to 8.2-8.4 with 1 M sodium carbonate (~1.6 mL) and the suspension was extracted with dichloromethane (2×15 mL) in a 30 mL separatory funnel. The aqueous layer was separated and acidified with 1 N HCl (1.7 mL) to pH 2.6-3.6. An aliquot (2 mL) of the predetermined volume of the aqueous solution (15-16 mL) was evaporated to dryness under reduced pressure on a rotary evaporator at 30-40° C. and the residue dissolved in 0.07% trifluoroacetic acid/water (200 uL). An aliquot of the solution was analyzed by HPLC, wherein an analyte in the effluent stream was quantified from its absorbance at 280 nm. The 14-hydroxycodeinone content of the sample was 8.7 ppm as determined from a plot of the area under the 2-(oxycodone-8-sulfanyl)-acetic acid peak per milligram of oxycodone analyzed versus the amount of 14-hydroxycodeinone added (ppm, i.e. micrograms of 14-hydroxycodeinone added per gram of oxycodone) as shown in FIG. 2. Control experiments indicated that the conversion of the thiol-Michael adduct contained in the analyte of this example (2-(oxycodone-8-sulfanyl)-ethanesulfonic acid) and contained in the analytes of other examples described herein, to the corresponding to the 2-(oxycodone-8-sulfanyl)-acetic acid thiol-Michael adduct during analytic determinations using sodium thioglycolate was negligible (<15%).

Plotted on the ordinate is the ratio of the area obtained for the peak corresponding to the thiol-Michael adduct 2-(oxycodone-8-sulfanyl)-acetic acid (14-HCA) and the weight of oxycodone (Oxy) analyzed (Area Units (AU)/mg). Plotted on the abscissa is the ratio of the weight of the 14-hydroxycodeinone (14-HC) spike and the weight of oxycodone analyzed (ppm).

EXAMPLE 7

Determination of the 2-(oxycodone-8-sulfanyl)-ethanesulfonic Acid Content of the Oxycodone Product of Example 5

The oxycodone product of EXAMPLE 5 (0.5 g, 1.6 mmol) was dissolved in dichloromethane (3 mL) and the solution was extracted once with water (3 mL). An aliquot (1 mL) of the aqueous extract was acidified with 1 N HCl (10 uL) and evaporated to dryness under reduced pressure on a rotary evaporator at 30-40° C. The residue was dissolved in 0.07% trifluoroacetic acid/water (200 uL) and the sample analyzed by HPLC, wherein an analyte in the effluent stream was quantified from its absorbance at 280 nm. The 2-(oxycodone-8-sulfanyl)-ethanesulfonic acid content of the oxycodone product produced in EXAMPLE 5 was thus determined to be 1.3 ppm.

EXAMPLE 8

Removal of 14-hydroxycodeinone from an Oxycodone Composition with 40 mM L-cysteine This example describes treatment of an oxycodone free base composition containing 3525 ppm of 14-hydroxycodeinone with 40 mM L-cysteine hydrochloride to effect (together with other operations) a more than 500-fold reduction in 14-hydroxycodeinone content of the composition and produce a product wherein the sum of the 14-hydroxycodeinone and the 2-(R)-amino-3-(oxycodone-8-sulfanyl)-propionic acid content was less than 10 ppm.

Oxycodone (5.0 g, 15.9 mmol) containing 3525 ppm of 14-hydroxycodeinone and L-cysteine hydrochloride hydrate (0.352 g, 2 mmol), chosen as a thiol-containing compound, were dissolved in 50 mL of 0.33 N HCl. The pH of the resulting solution was raised to 6.0-6.1 by addition of 1 M sodium carbonate with stirring to dissolve any precipitated oxycodone. The resulting solution was stirred for 1 h and then solid sodium carbonate (1.6 g, 15.1 mmol) was added to the solution with vigorous stirring. After ~7 min (the pH of the solution increased to approximately 7.6), the oxycodone suspension was extracted into ethyl acetate (250 mL), and the ethyl acetate extract was vigorously stirred with 50 mL of aqueous 40 mM L-cysteine (pH 8.0) for 45 min. After removal of the L-cysteine wash, the ethyl acetate solution of oxycodone was washed with 50 mL of water and stirred with 50 mL of 0.33 N HCl for 10 min to extract the oxycodone into the aqueous acid. The aqueous layer was separated and the pH was raised to 9.1-9.3 with 1 M sodium carbonate (~22 mL) to precipitate oxycodone free base. The precipitate was collected, washed with 25 mL of water, and dried in a desiccator under reduced pressure to yield 4.65 g (93% yield) of an oxycodone product, wherein the sum of the 14-hydroxycodeinone and the 2-(R)-amino-3-(oxycodone-8-sulfanyl)-propionic acid (thiol-Michael adduct) content was less than 5 ppm (see EXAMPLES 9-10).

EXAMPLE 9

Determination of the 14-hydroxycodeinone Content of the Oxycodone Product of Example 8

Figure 3:
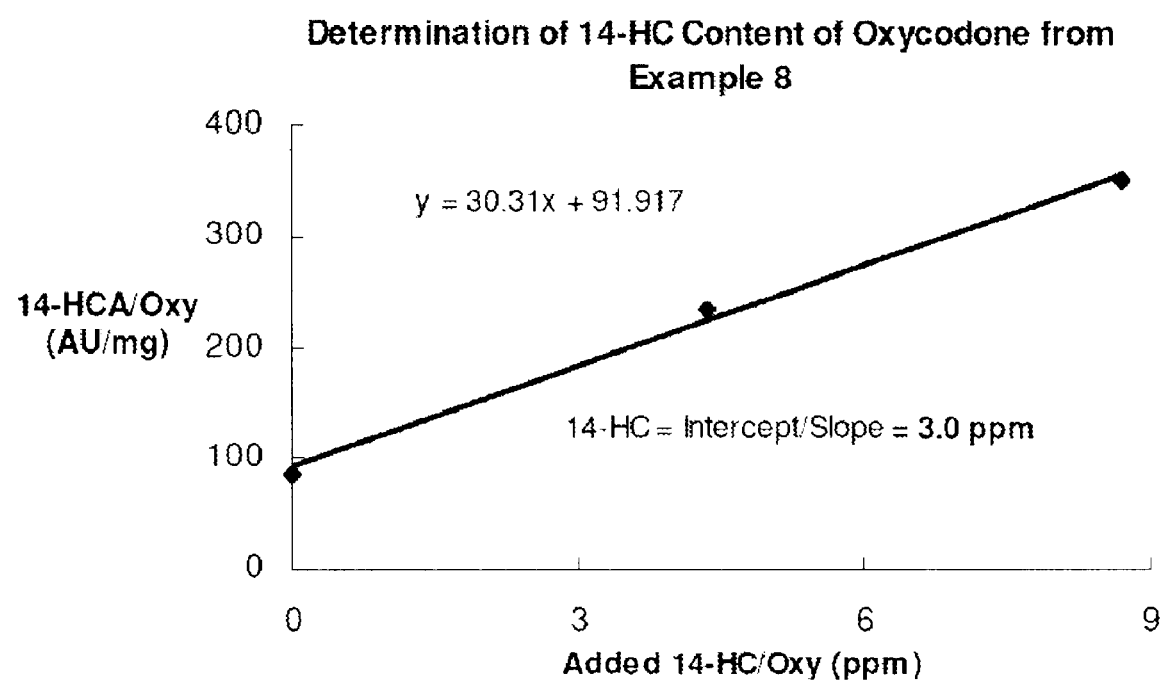
FIG. 3 depicts a plot used to determine the 14-hydroxycodeinone (14-HC) content of the oxycodone product of Example 8 with sodium thioglycolate.

The oxycodone product of EXAMPLE 8 (0.5 g, 1.6 mmol) was dissolved in 0.2 N HCl (10 mL). EDTA (0.005 g, 0.017 mmol) was added and the solution pH was raised to 6.0-6.3 with 1 M sodium carbonate with stirring to dissolve any precipitated oxycodone. To the homogeneous reaction mixture was added sodium thioglycolate (0.025 g, 0.22 mmol). In separate spike experiments known amounts of 14-hydroxycodeinone were introduced prior to addition of sodium thioglycolate. After 1 h the pH of the solution was raised to 8.1-8.6 with 1 M sodium carbonate (~1.4-1.5 mL) and the suspension was extracted with dichloromethane (2×15 mL) in a 30 mL separatory funnel. The aqueous layer was separated and acidified with 1 N HCl (1.5-1.7 mL) to pH 3.2-3.8. An aliquot (2 mL) of the predetermined volume of the aqueous solution (14 mL) was evaporated to dryness under reduced pressure on a rotary evaporator at 30-40° C. and the residue dissolved in 0.07% trifluoroacetic acid/water (400 uL). An aliquot of the solution was analyzed by HPLC, wherein an analyte in the effluent stream was quantified from its absorbance at 280 nm. The 14-hydroxycodeinone content of the sample was 3.0 ppm as determined from a plot of the area under the 2-(oxycodone-8-sulfanyl)-acetic acid peak per milligram of oxycodone analyzed versus the amount of 14-hydroxycodeinone added (ppm, i.e. micrograms of 14-hydroxycodeinone added per gram of oxycodone) as shown in FIG. 3.

Plotted on the ordinate is the ratio of the area obtained for the peak corresponding to the thiol-Michael adduct 2-(oxycodone-8-sulfanyl)-acetic acid (14-HCA) and the weight of oxycodone (Oxy) analyzed (Area Units (AU)/mg). Plotted on the abscissa is the ratio of the weight of the 14-hydroxycodeinone (14-HC) spike and the weight of oxycodone analyzed (ppm).

EXAMPLE 10

Determination of the 2-(R)-amino-3-(oxycodone-8-sulfanyl)-propionic Acid Content of the Oxycodone Product of Example 8

The oxycodone product of EXAMPLE 8 (0.5 g, 1.6 mmol) was dissolved in dichloromethane (3 mL) and the solution was extracted once with water (3 mL). An aliquot (1 mL) of the aqueous extract was acidified with 1 N HCl (10 uL) and evaporated to dryness under reduced pressure on a rotary evaporator at 30-40° C. The residue was dissolved in 0.07% trifluoroacetic acid/water (200 uL) and the sample analyzed by HPLC, wherein an analyte in the effluent stream was quantified from its absorbance at 280 nm. The 2-(R)-amino-3-(oxycodone-8-sulfanyl)-propionic acid content of the oxycodone product produced in EXAMPLE 8 was thus determined to be 1.6 ppm.

EXAMPLE 11

Removal of 14-hydroxycodeinone Content from an Oxycodone Composition with Thiol Functionalized Silica Gel This example describes treatment of an oxycodone free base composition containing 3525 ppm of 14-hydroxycodeinone with a commercially available thiol functionalized silica (wherein a 3-mercaptopropanol moiety has been covalently linked to silica) to effect (together with other operations) a more than 500-fold reduction in 14-hydroxycodeinone content of the composition and produce a product wherein the 14-hydroxycodeinone content was less than 5 ppm.

Oxycodone (2.0 g, 6.3 mmol) containing 3535 ppm of 14-hydroxycodeinone was dissolved in 80 mL of 0.08 N HCl. The pH of the resulting solution was raised to 7.0-7.05 by addition of 2 N sodium hydroxide with stirring. After dissolution of any oxycodone that precipitated during the addition of sodium hydroxide, thiol functionalized silica gel, (1 g, loading-1.44 mmol/g) used as the thiol-containing compound (1 g, loading-1.44 mmol/g) was added. The resulting solution was stirred for 17.5 h and then filtered. The pH of the aqueous layer was raised to 9.2 with 1 M sodium carbonate (~7 mL) to precipitate oxycodone free base. The precipitate was collected, washed with 10 mL of water, and dried in a desiccator under reduced pressure to yield 1.89 g (94.5% yield) of an oxycodone product, wherein the 14-hydroxycodeinone content was less than 5 ppm (see EXAMPLE 12).

EXAMPLE 12

Determination of the 14-hydroxycodeinone Content of the Oxycodone Product of Example 11

Figure 4:
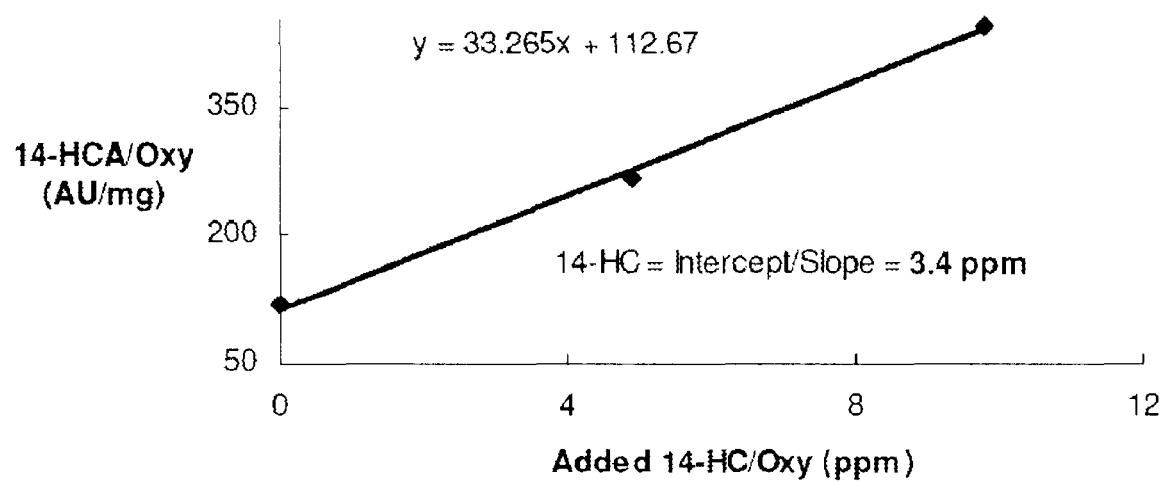
FIG. 4 depicts a plot used to determine the 14-hydroxycodeinone (14-HC) content of the oxycodone product of Example 11 with sodium thioglycolate.

The oxycodone product of EXAMPLE 11 (0.5 g, 1.6 mmol) was dissolved in 0.2 N HCl (10 mL). EDTA (0.005 g, 0.017 mmol) was added and the solution pH was raised to 6.0-6.2 with 1 M sodium carbonate with stirring to dissolve any precipitated oxycodone. To the homogeneous reaction mixture was added sodium thioglycolate (0.025 g, 0.22 mmol). In separate spike experiments known amounts of 14-hydroxycodeinone were introduced prior to addition of sodium thioglycolate. After 1 h, the pH of the solution was raised to 8.0-8.3 with 1 M sodium carbonate (~1.5-1.6 mL) and the suspension was extracted with dichloromethane (2×15 mL) in a 30 mL separatory funnel. The aqueous layer was separated and acidified with 1 N HCl (1.6-1.7 mL) to pH 2.5-3.4. An aliquot (2 mL) of the predetermined volume of the aqueous solution (15 mL) was evaporated to dryness under reduced pressure on a rotary evaporator at 30-40° C. and the residue dissolved in 0.07% trifluoroacetic acid/water (400 uL). An aliquot of the solution was analyzed by HPLC, wherein an analyte in the effluent stream was quantified from its absorbance at 280 nm. The 14-hydroxycodeinone content of the sample was 3.4 ppm as determined from a plot of the area under the 2-(oxycodone-8-sulfanyl)-acetic acid peak per milligram of oxycodone analyzed versus the amount of 14-hydroxycodeinone added (ppm, i.e. micrograms of 14-hydroxycodeinone added per gram of oxycodone) as shown in FIG. 4.

Plotted on the ordinate was the ratio of the area obtained for the peak corresponding to the thiol-Michael adduct 2-(oxycodone-8-sulfanyl)-acetic acid (14-HCA) and the weight of oxycodone (Oxy) analyzed (Area Units (AU)/mg). Plotted on the abscissa is the ratio of the weight of the 14-hydroxycodeinone (14-HC) spike and the weight of oxycodone analyzed (ppm).

EXAMPLE 13

Removal of 14-hydroxycodeinone of an Oxycodone Composition with 20 mM N-acetyl-L-cysteine This example describes treatment of an oxycodone free base composition containing 3525 ppm of 14-hydroxycodeinone with 20 mM N-acetyl-L-cysteine to effect (together with other operations) a more than 500-fold reduction in 14-hydroxycodeinone content of the composition and produce a product wherein the 14-hydroxycodeinone content was less than 5 ppm.

Oxycodone (5.0 g, 15.9 mmol) containing 3525 ppm of 14-hydroxycodeinone and N-acetyl-L-cysteine, a thiol-containing compound, (0.163 g, 1 mmol) were dissolved in 50 mL of 0.32 N HCl. The pH of the resulting solution was raised to 6.0-6.1 by addition of 1 M sodium carbonate with stirring to dissolve any precipitated oxycodone. The resulting solution was stirred for 1 h and then solid sodium carbonate (1.6 g, 15.1 mmol) was added to the solution with vigorous stirring. After ~6 min (the pH of the solution increased to approximately 8.0), the oxycodone suspension was extracted into ethyl acetate (250 mL), and the ethyl acetate extract was vigorously stirred with 50 mL of aqueous 20 mM N-acetyl-L-cysteine (pH 8.0) for 20 min. After removal of the N-acetyl-L-cysteine wash, the ethyl acetate solution of oxycodone was washed with 50 mL of water and stirred with 50 mL of 0.34 N HCl for 10 min to extract the oxycodone into the aqueous acid. The aqueous layer was separated and the pH was raised to 9.1-9.2 with 1 M sodium carbonate (~22 mL) to precipitate oxycodone free base. The precipitate was collected, washed with 25 mL of water, and dried in a desiccator under reduced pressure to yield 4.7 g (94% yield) of an oxycodone product, wherein the 14-hydroxycodeinone (thiol-Michael adduct) content was less than 5 ppm (see EXAMPLE 14).

EXAMPLE 14

Determination of the 14-hydroxycodeinone Content of the Oxycodone Product of Example 13

Figure 5:
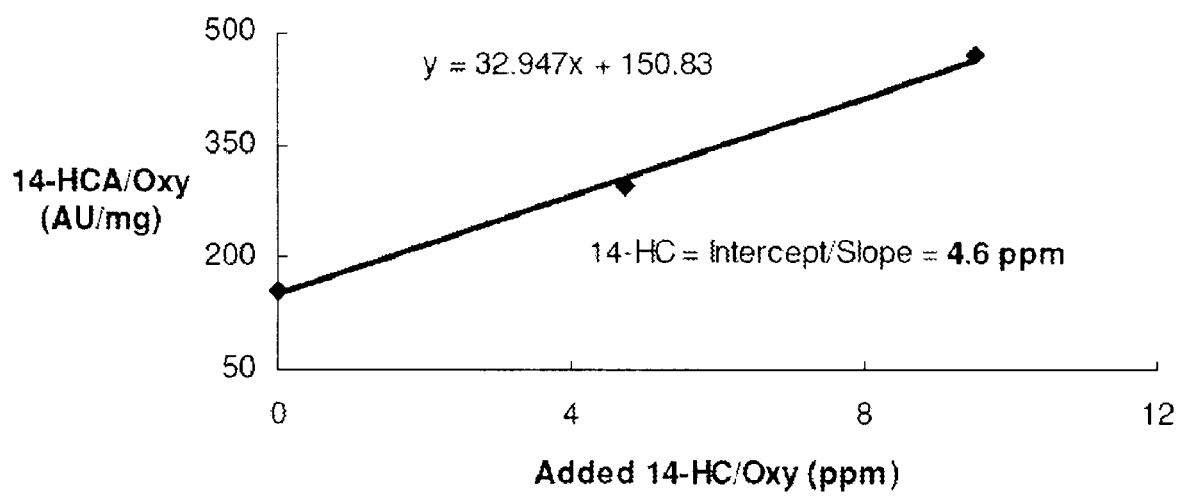
FIG. 5 depicts a plot used to determine the 14-hydroxycodeinone (14-HC) content of the oxycodone product of Example 13 with sodium thioglycolate.

The oxycodone product of EXAMPLE 13 (0.5 g, 1.6 mmol) was dissolved in 0.2 N HCl (10 mL). EDTA (0.005 g, 0.017 mmol) was added and the solution pH was raised to 6.0-6.2 with 1 M sodium carbonate with stirring to dissolve any precipitated oxycodone. To the homogeneous reaction mixture was added sodium thioglycolate (0.025 g, 0.22 mmol). In separate spike experiments known amounts of 14-hydroxycodeinone were introduced prior to addition of sodium thioglycolate. After 1 h, the pH of the solution was raised to 8.2 with 1 M sodium carbonate (~1.5 mL) and the suspension was extracted with dichloromethane (2×15 mL) in a 30 mL separatory funnel. The aqueous layer was separated and acidified with 1 N HCl (1.6 mL) to pH 3.5-3.7. An aliquot (2 mL) of the predetermined volume of the aqueous solution (15-16 mL) was evaporated to dryness under reduced pressure on a rotary evaporator at 30-40° C. and the residue dissolved in 0.07% trifluoroacetic acid/water (400 uL). An aliquot of the solution was analyzed by HPLC, wherein an analyte in the effluent stream was quantified from its absorbance at 280 nm. The 14-hydroxycodeinone content of the sample was 4.6 ppm as determined from a plot of the area under the 2-(oxycodone-8-sulfanyl)-acetic acid peak per milligram of oxycodone analyzed versus the amount of 14-hydroxycodeinone added (ppm, i.e. micrograms of 14-hydroxycodeinone added per gram of oxycodone) as shown in FIG. 5.

Plotted on the ordinate is the ratio of the area obtained for the peak corresponding to the thiol-Michael adduct 2-(oxycodone-8-sulfanyl)-acetic acid (14-HCA) and the weight of oxycondone (Oxy) analyzed (Area Units (AU)/mg). Plotted on the abscissa is the ratio of the weight of the 14-hydroxycodeinone (14-HC) spike and the weight of oxycodone analyzed (ppm).

EXAMPLE 15

Removal of the 14-hydroxycodeinone from an Oxycodone Composition with 40 mM Sodium 2-mercaptoethanesulfonate This example describes treatment of an oxycodone free base composition containing 3525 ppm of 14-hydroxycodeinone with 40 mM sodium 2-mercaptoethanesulfonate to effect (together with other operations) a more than 300-fold reduction in 14-hydroxycodeinone content of the composition and produce a product wherein the sum of the 14-hydroxycodeinone and the 2-(oxycodone-8-sulfanyl)-ethanesulfonic acid content was less than 10 ppm.

Oxycodone (5.0 g, 15.9 mmol) containing 3525 ppm of 14-hydroxycodeinone was dissolved in 50 mL of 0.33 N HCl. The pH of the resulting solution was raised to 6.2 by addition of 1 M sodium carbonate with stirring. After dissolution of any oxycodone that precipitated during the addition of the sodium carbonate, sodium 2-mercaptoethanesulfonate (0.33 g, 2 mmol) was added, the resulting solution stirred for 1 h and solid sodium carbonate (1.5 g, 14.2 mmol) then added to the solution with vigorous stirring. After ~6 min (the pH of the solution increased to approximately 7.8), the oxycodone suspension was extracted into ethyl acetate (250 mL), and the ethyl acetate extract was vigorously stirred with 50 mL of the aqueous 20 mM sodium 2-mercaptoethanesulfonate solution for 20 min. After removal of the sodium 2-mercaptoethanesulfonate wash, the ethyl acetate solution of oxycodone was washed with 50 mL of water and stirred with 50 mL of 0.34 N HCl for 10 min to extract the oxycodone into the aqueous acid. The aqueous layer was separated and the pH was raised to 9.2-9.3 with 1 M sodium carbonate (~22 mL) to precipitate oxycodone free base. The precipitate was collected, washed with 25 mL of water, and dried in a desiccator under reduced pressure to yield 4.66 g (93.2% yield) of an oxycodone product, the sum of the 14-hydroxycodeinone content and the 2-(oxycodone-8-sulfanyl)-ethanesulfonic acid content was less than 10 ppm (see EXAMPLES 16-17).

EXAMPLE 16

Determination of the 14-hydroxycodeinone content of the Oxycodone Product of Example 15

Figure 6:
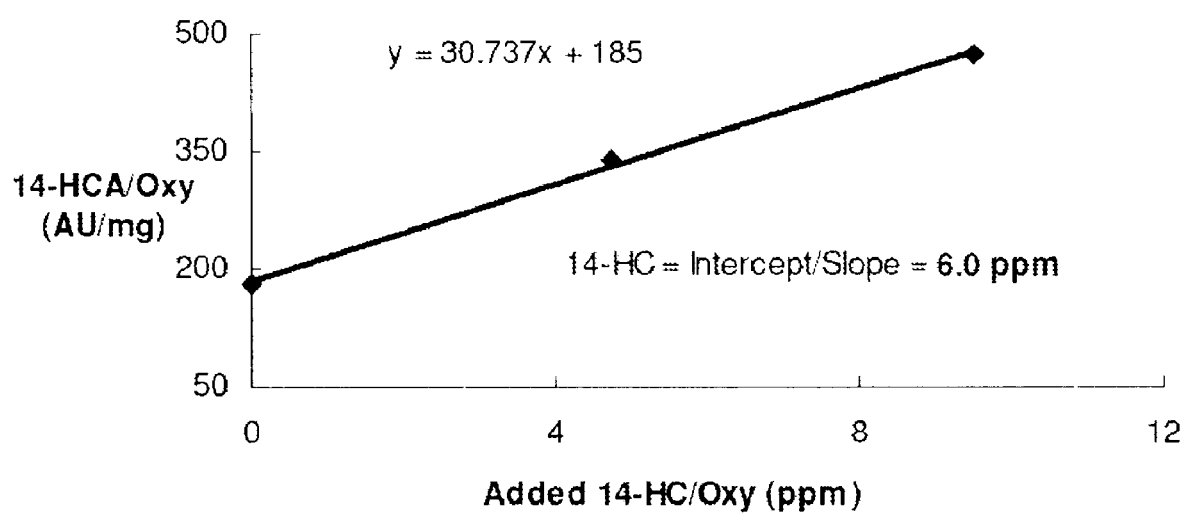
FIG. 6 depicts a plot used to determine the 14-hydroxycodeinone (14-HC) content of the oxycodone product of Example 15 with sodium thioglycolate.

The oxycodone product of EXAMPLE 15 (0.5 g, 1.6 mmol) was dissolved in 0.2 N HCl (10 mL). EDTA (0.005 g, 0.017 mmol) was added and the solution pH was raised to 6.1-6.2 with 1 M sodium carbonate with stirring to dissolve any precipitated oxycodone. To the homogeneous reaction mixture was added sodium thioglycolate (0.025 g, 0.22 mmol). In separate spike experiments known amounts of 14-hydroxycodeinone were introduced prior to addition of sodium thioglycolate. After 1 h, the pH of the solution was raised to 8.2-8.4 with 1 M sodium carbonate (~1.5 mL) and the suspension was extracted with dichloromethane (2×15 mL) in a 30 mL separatory funnel. The aqueous layer was separated and acidified with 1 N HCl (1.6 mL) to pH 3.2-3.5. An aliquot (2 mL) of the predetermined volume of the aqueous solution (14.5-16 mL) was evaporated to dryness under reduced pressure on a rotary evaporator at 30-40° C. and the residue dissolved in 0.07% trifluoroacetic acid/water (400 uL). An aliquot of the solution was analyzed by HPLC, wherein an analyte in the effluent stream was quantified from its absorbance at 280 nm. The 14-hydroxycodeinone content of the sample was 6.0 ppm as determined from a plot of the area under the 2-(oxycodone-8-sulfanyl)-acetic acid peak per milligram of oxycodone analyzed versus the amount of 14-hydroxycodeinone added (ppm, i.e. micrograms of 14-hydroxycodeinone added per gram of oxycodone) as shown FIG. 6.

Plotted on the ordinate is the ratio of the area obtained for the peak corresponding to the thiol-Michael adduct 2-(oxycodone-8-sulfanyl)-acetic acid (14-HCA) and the weight of oxycodone (Oxy) analyzed (Area Units (AU)/mg). Plotted on the abscissa is the ratio of the weight of the 14-hydroxycodeinone (14-HC) spike and the weight of oxycodone analyzed (ppm)

EXAMPLE 17

Determination of the 2-(oxycodone-8-sulfanyl)-ethanesulfonic Acid Content of the Oxycodone Product of Example 15

The oxycodone product of EXAMPLE 15 (0.5 g, 1.6 mmol) was dissolved in dichloromethane (3 mL) and the solution was extracted once with water (3 mL). An aliquot (1 mL) of the aqueous extract was acidified with 1 N HCl (10 uL) and evaporated to dryness under reduced pressure on a rotary evaporator at 30-40° C. The residue was dissolved in 0.07% trifluoroacetic acid/water (200 uL) and the sample analyzed by HPLC, wherein an analyte in the effluent stream was quantified from its absorbance at 280 nm. The 2-(oxycodone-8-sulfanyl)-ethanesulfonic acid content of the oxycodone product produced in EXAMPLE 15 was thus determined to be 1.6 ppm.

EXAMPLE 18

Reduction of the 7,8-dehydronaltrexone Content of Naltrexone

This example describes the reduction of the 7,8-dehydronaltrexone content of naltrexone by more than 300-fold and production of a naltrexone product wherein the 7,8-dehydronaltrexone content was less than 5 ppm by treatment of naltrexone in water with sodium thioglycolate.

Naltrexone (2.0 g, 5.9 mmol) containing 690 ppm of 7,8-dehydronaltrexone was dissolved in 20 mL of 0.3 N HCl. The pH of the resulting solution was raised to 6.15 by addition of 1 M sodium carbonate with stirring. After dissolution of any naltrexone that precipitated during the addition of sodium carbonate, sodium thioglycolate (0.046 g, 0.4 mmol) was added. The resulting solution was stirred for 1 h and then solid sodium carbonate (0.6 g, 5.7 mmol) was added to the solution with vigorous stirring. After ~8 min (the pH of the solution increased to approximately 8.1-8.2), the naltrexone suspension was extracted into ethyl acetate (100 mL), and the ethyl acetate extract was vigorously stirred with 20 mL of aqueous 20 mM sodium thioglycolate for 20 min. After removal of the sodium thioglycolate wash, the ethyl acetate solution of naltrexone was washed with 20 mL of water and stirred with 20 mL of 0.34 N HCl for 10 min to extract naltrexone into the aqueous acid. The aqueous layer was separated and the pH was raised to 8.8-8.9 with 1 M sodium carbonate (~7.5 mL) to precipitate naltrexone. The precipitate was collected, washed with 4 mL of water, and dried in a desiccator under reduced pressure to yield 1.95 g (97.5% yield) of a naltrexone product, wherein the 7,8-dehydronaltrexone content was less than 5 ppm (see EXAMPLE 19).

EXAMPLE 19

Determination of the 7,8-dehydronaltrexone Content of the Naltrexone Product of Example 18

The naltrexone product of EXAMPLE 18 (0.5 g, 1.47 mmol) was dissolved in 0.2 N HCl (10 mL). EDTA (0.005 g, 0.017 mmol) was added and the solution pH was raised to 6.0 with 1 M sodium carbonate with stirring to dissolve any precipitated naltrexone. To the homogeneous reaction mixture was added sodium thioglycolate (0.025 g, 0.22 mmol). After 1 h the pH of the solution was raised to 8.9 with 1 M sodium carbonate (~1.5 mL) and the suspension was extracted with dichloromethane (2×15 mL) in a 30 mL separatory funnel. The aqueous layer was separated and acidified with 1 N HCl (1.6 mL). An aliquot (2 mL) of the predetermined volume of the aqueous solution (15-16 mL) was evaporated to dryness under reduced pressure on a rotary evaporator at 30-40° C. and the residue dissolved in 0.07% trifluoroacetic acid/water (400 uL). An aliquot of the solution was analyzed by HPLC, wherein an analyte in the effluent stream was quantified from its absorbance at 280 nm. The 7,8-dehydronaltrexone content was ~1 ppm.

EXAMPLE 20

Figure 7:
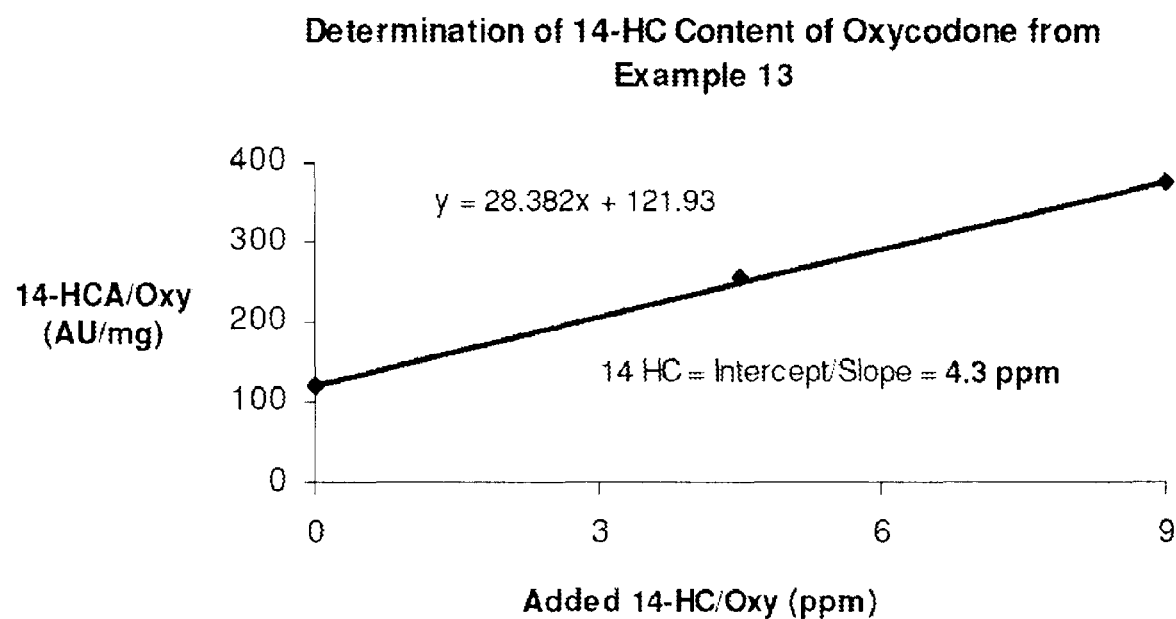
FIG. 7 depicts a plot used to determine the 14-hydroxycodeinone (14-HC) content of the oxycodone product of Example 13 with sodium thioglycolate using reduced amounts of sample.

Determination of the 14-hydroxycodeinone Content of an Oxycodone Product Using a Reduced Amount of Sample The following procedure represents a modification of the procedure described in EXAMPLE 14 that was designed for use when the amount of oxycodone product available for analysis was limited. The oxycodone product of EXAMPLE 13 (100 mg, 0.317 mmol) was placed in an 8 mL reaction vial, one that accommodates a threaded, Teflon-lined cap and small magnetic stir bar, and dissolved in 0.2 N HCl (2 mL). EDTA (0.001 g, 0.0034 mmol) was added and the solution pH was raised to 6.0-6.2 by addition of 1 M aqueous sodium carbonate with stirring to dissolve any precipitated oxycodone. Determination of pH was accomplished using a pH meter with a sufficiently narrow combination electrode (~5 mm) so as to allow its insertion directly into the sample vial. To the homogeneous reaction mixture was added sodium thioglycolate (0.005 g, 0.044 mmol); in separate spike experiments, known amounts of 14-hydroxycodeinone were introduced prior to addition of sodium thioglycolate. After 1 h, the pH of the solution was raised to 8.2 with 1 M aqueous sodium carbonate (~0.07 mL) and the suspension was extracted with dichloromethane (2×3 mL) by adding the solvent to the vial, capping it, and shaking it vigorously. The organic layer was removed from the vial by Pasteur pipet. The aqueous layer was acidified with 1 N HCl (0.3 mL) and the solution reduced to dryness via rotary evaporation (bath temp 30-40° C.). The residue was dissolved in 0.07% trifluoroacetic acid/water (400 uL) and an aliquot of the solution was analyzed by HPLC, wherein an analyte in the effluent stream was quantified from its absorbance at 280 nm. The 14-hydroxycodeinone content of the sample was 4.3 ppm as determined from a plot of the area under the 2-(oxycodone-8-sulfanyl)-acetic acid peak per milligram of oxycodone analyzed versus the amount of 14-hydroxycodeinone added (ppm, i.e. micrograms of 14-hydroxycodeinone added per gram of oxycodone) as shown in FIG. 7. The 14-hydroxycodeinone content determined by this method (4.3 ppm) was within 10 percent of the determination made for the same sample as described in EXAMPLE 14 (4.6 ppm).

Plotted on the ordinate is the ratio of the area obtained for the peak corresponding to the thiol-Michael adduct 2-(oxycodone-8-sulfanyl)-acetic acid (14-HCA) and the weight of oxycodone (Oxy) analyzed (Area Units (AU)/mg). Plotted on the abscissa is the ratio of the weight of the 14-hydroxycodeinone (14-HC) spike and the weight of oxycodone analyzed, in ppm.

EXAMPLE 21

Figure 8:
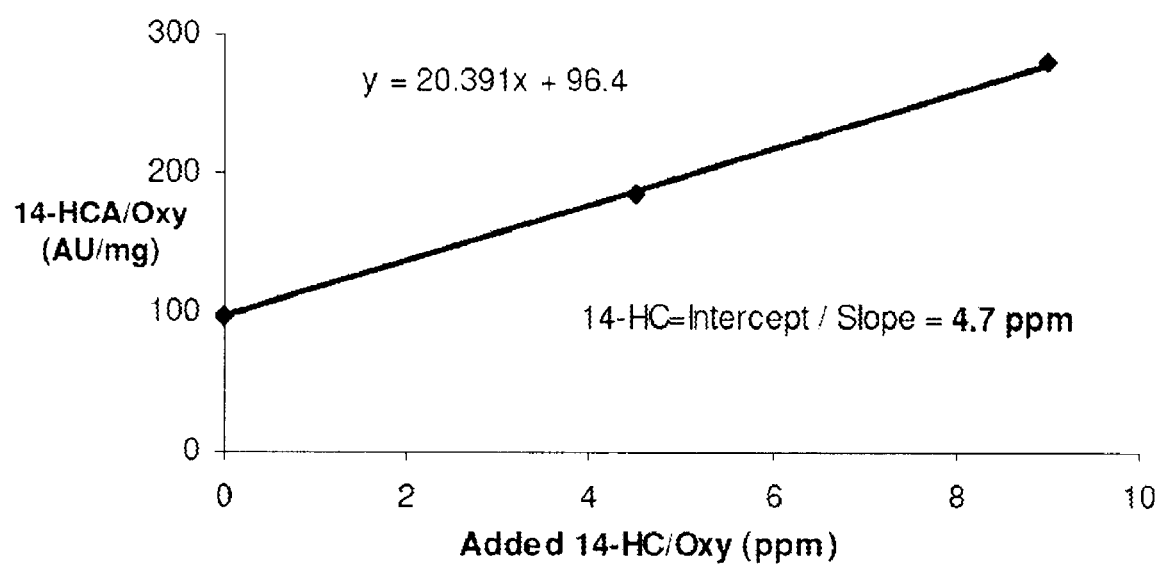
FIG. 8 depicts a plot used to determine the 14-hydroxycodeinone (14-HC) content of the oxycodone product of Example 13 with 5-mercapto-2-nitro-benzoic acid.

Determination of the 14-hydroxycodeinone Content of the Oxycodone Product of Example 13 with 5-mercapto-2-nitro-benzoic Acid The oxycodone product of EXAMPLE 13 (0.300 g, 0.952 mmol) was suspended in 0.2 N aqueous HCl (3 mL) in an 8 mL reaction vial—one that accommodates a threaded, Teflon-lined cap and small magnetic stir bar. Concentrated HCl was added (30 uL), dissolving the solid completely, and the pH was raised to 4.5 by addition of 100 mg/mL aqueous $Na_2HPO_4$ solution (0.11 mL) and 1 N aqueous HCl (0.05 mL). Determination of pH was accomplished using a pH meter with a sufficiently narrow combination electrode (~5 mm) so as to allow its insertion directly into the sample vial. An aliquot of this solution (1 mL) was diluted with pH 4.5 0.05 M aqueous NaOAc/HOAc buffer (0.1 mL) and set aside; the remainder was reserved for separate spike experiments where known amounts of 14-hydroxycodeinone were added prior to the next step. In a separate reaction vessel, 5,5'-dithiobis(2-nitro-benzoic acid) (10 mg, 0.025 mmol) was completely dissolved in pH 7 0.05 M aqueous sodium phosphate buffer solution (5 mL). EDTA (5 mg) and dithiothreitol (2.0 mg, 0.013 mmol) were added and the pH of the resulting orange-colored solution was raised to 6.8 with 100 mg/mL aqueous $Na_2HPO_4$ solution (0.45 mL). After stirring for 30 minutes, the pH was lowered to 4.7 with 25% aqueous acetic acid solution (0.105 mL) and an aliquot of this solution (1 mL) was added to the vial containing the previously prepared oxycodone solution. After stirring for 90 minutes, the pH of the combined solution was lowered to 2 with concentrated HCl (15 uL) and the resulting suspension extracted with dichloromethane (4×2 mL) by adding the solvent to the vial, capping it, and shaking vigorously. The organic layer was completely removed from the vial by Pasteur pipet. The aqueous layer was analyzed by HPLC, wherein an analyte in the effluent stream was quantified from its absorbance at 325 nm. The 14-hydroxycodeinone content of the sample was 4.7 ppm as determined from a plot of the area under the 2-nitro-5-(oxycodone-8-sulfanyl)-benzoic acid peak per milligram of oxycodone analyzed versus the amount of 14-hydroxycodeinone added (ppm, i.e. micrograms of 14-hydroxycodeinone added per gram oxycodone) as shown in FIG. 8. The 14-hydroxycodeinone content determined by this method (4.7 ppm) was within 10 percent of the determination made for the same sample as described in EXAMPLE 14 (4.6 ppm).

Plotted on the ordinate is the ratio of the area obtained for the peak corresponding to the thiol-Michael adduct 2-nitro-(5-(oxycodone-8-sulfanyl)-benzoic acid (14-HCA) and the weight of oxycodone (Oxy) analyzed (Area Units (AU)/mg). Plotted on the abscissa is the ratio of the weight of the 14-hydroxycodeinone (14-HC) spike and the weight of oxycodone analyzed, in ppm.

EXAMPLE 22

Figure 9:
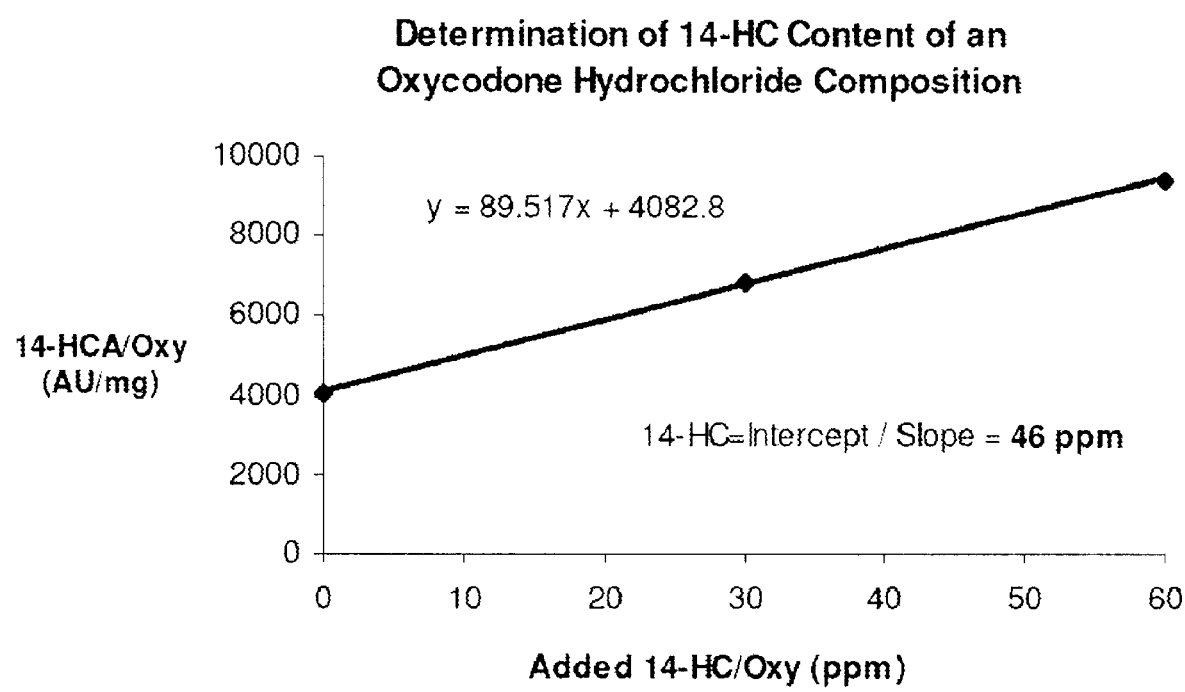
FIG. 9 depicts a plot used to determine the 14-hydroxycodeinone (14-HC) content of an oxycodone hydrochloride composition with 5-mercapto-2-nitro-benzoic acid.

Determination of the 14-hydroxycodeinone Content of an Oxycodone Hydrochloride Composition with 5-mercapto-2-nitro-benzoic Acid In an 8 mL reaction vial, one that accommodates a threaded, Teflon-lined cap and small magnetic stir bar, a pH 7.4 buffer was prepared by dissolving 5 mg of EDTA in 0.1 M aqueous $Na_2HPO_4$ solution (4.75 mL) and 0.1 M aqueous $NaH_2PO_4$ solution (0.25 mL). Dithiothreitol (2.1 mg, 0.014 mmol) was added followed by 5,5'-dithiobis(2-nitro-benzoic acid) (9.8 mg, 0.025 mmol) which immediately turned the solution color orange. When the solid completely dissolved (5 minutes), the pH of the solution was lowered to 4.5 with 1 N aqueous HCl solution (0.35 mL). Determination of pH was accomplished using a pH meter with a sufficiently narrow combination electrode (~5 mm) so as to allow its insertion directly into the sample vial. Oxycodone hydrochloride (482 mg, 1.37 mmol) was placed in a separate 8 mL reaction vial, to which was added 3.0 mL of the previously prepared solution. The pH of the mixture was lowered to 4.5 by addition of 1 N aqueous HCl solution (10 uL), and a 1.0 mL aliquot was removed and stirred. The remainder was reserved for separate spike experiments where known amounts of 14-hydroxycodeinone were added to the mixture. After 90 minutes, the pH was lowered to 2 with concentrated HCl (10 uL) and the suspension extracted with dichloromethane (4×1 mL) by adding the solvent to the vial, capping it, and shaking vigorously. The organic layer was completely removed from the vial by Pasteur pipet. The aqueous layer was analyzed by HPLC, wherein an analyte in the effluent stream was quantified from its absorbance at 325 nm. The 14-hydroxycodeinone content of the sample was 46 ppm as determined from a plot of the area under the 2-nitro-5-(oxycodone-8-sulfanyl)-benzoic acid peak per milligram of oxycodone analyzed versus the amount of 14-hydroxycodeinone added (ppm, i.e. micrograms of 14-hydroxycodeinone added per gram of oxycodone) as shown in FIG. 9.

Plotted on the ordinate is the ratio of the area obtained for the peak corresponding to the thiol-Michael adduct 5-(oxycodone-8-sulfanyl)-2-nitro-benzoic acid (14-HCA) and the weight of oxycodone (Oxy) analyzed (Area Units (AU)/mg). Plotted on the abscissa is the ratio of the weight of the 14-hydroxycodeinone (14-HC) spike and the weight of oxycodone analyzed, in ppm.

EXAMPLE 23

Use of N-dansyl-L-cysteine to Determine the 14-hydroxycodeinone Content of a Oxycodone-Hydrochloride Processed Product that was Prepared by Removing 14-hydroxycodeinone (with 20 mM thioglycolate) from the Composition Analyzed in Example 22

Figure 10:
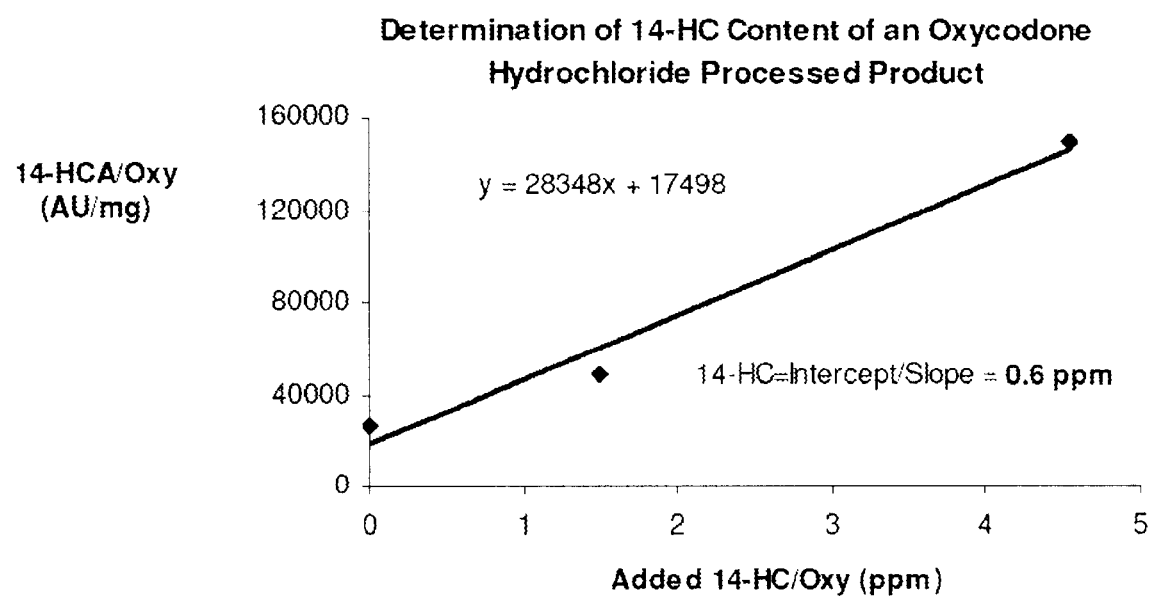
FIG. 10 depicts a plot used to determine the 14-hydroxycodeinone (14-HC) content of the oxycodone hydrochloride product of Example 22 with N-dansyl-L-cysteine.

In a 25 mL round-bottom reaction flask equipped with a magnetic stir bar, the following were added: 10 mL of a pH 7.0, 50 mM phosphate buffer; EDTA (2 mg, 0.007 mmol); dithiothreitol (3.1 mg, 0.020 mmol); N,N'-didansyl-L-cystine (28 mg, 0.038 mmol). The pH of the resulting solution was raised to 7.0 with 10% aqueous disodium phosphate (0.5 mL), and the solution stirred for 1 h. A 3.5 mL aliquot of the solution was then added to an 8 mL reaction vial containing oxycodone hydrochloride (230 mg, 0.65 mmol). The pH of the resulting oxycodone solution was raised to 6.1-6.2 by addition of 10% aqueous disodium phosphate (0.2 mL). An aliquot (1.2 mL) was removed and placed in an 8 mL reaction vial. The remainder was reserved for separate spike experiments. After 90 minutes, the pH of the reaction mixture was lowered to 2.4-2.5 with 1 N HCl, and the resulting solution extracted with once with ethyl acetate (1.5 mL). The aqueous phase was analyzed by HPLC wherein an analyte in the effluent stream was quantified from its fluorescence at 530 nm. The 14-hydroxycodeinone content of the sample was 0.6 ppm as determined from a plot of the area under the 2-(R)-(5-dimethylamino-naphthalene-1-sulfonylamino)-3-(oxycodone-8-sulfanyl)-propionic acid peak per milligram of oxycodone analyzed versus the amount of 14-hydroxycodeinone added (ppm, i.e. micrograms of 14-hydrocodeinone added per gram of oxycodone) as shown in FIG. 10.

Plotted on the ordinate is the ratio of the area obtained for the peak attributed to the thiol-Michael adduct 2-(R)-(5-dimethylamino-naphthalene-1-sulfonylamino)-3-(oxycodone-8-sulfanyl)-propionic acid (14-HCA) and the weight of oxycodone (Oxy) analyzed (Emission Units (EU)/mg). Plotted on the abscissa is the ratio of the weight of the 14-hydroxycodeinone (14-HC) spike and the weight of oxycodone analyzed, in ppm.

EXAMPLE 24

Determination of the 8-hydroxyoxycodone Content of an Oxycodone Composition Containing Less Than 1 ppm of 14-hydroxycodeinone This example describes a process for determination of the 8-hydroxyoxycodone content of an oxycodone composition containing less than 1 ppm of 14-hydroxycodeinone wherein the Michael acceptor precursor 8-hydroxyoxycodone was converted to 14-hydroxycodeinone, and the 14-hydroxycodeinone content of the resulting product was determined and related to the 8-hydroxycodone content of the original oxycodone composition.

In a 500 mL round-bottom flask, equipped with a reflux condenser, oxycodone (1.50 g, 4.76 mmol) and p-toluenesulfonic acid monohydrate (1.52 g, 8.0 mmol) were dissolved in toluene (300 mL) and heated to reflux. After 2.5 hours, the toluene was removed under reduced pressure at 35-40° C. by rotary evaporation. The resulting residue was dissolved in water (100 mL) and the pH adjusted to 9 by addition of solid sodium carbonate (1.25 g). The aqueous solution was extracted with dichloromethane (3×30 mL), the combined organic layers were dried over anhydrous sodium sulfate and filtered, and the solvent was removed via rotary evaporation. The resulting white solid was further dried under reduced pressure to give oxycodone (1.37 g, 91%).

Determination of the 14-hydroxycodeinone content of the oxycodone product using the method described in EXAMPLE 20 indicated 85 ppm of 14-hydroxycodeinone. This result together with the separately determined >98% conversion of 8-hydroxyoxycodone to 14-hydroxycodeinone under the conditions used to effect dehydration indicates that the original oxycodone composition contained ~85 ppm of 8-hydroxyoxycodone.

EXAMPLE 25

Removal of 8-hydroxyoxycodone from an Oxycodone Composition

This example describes a process for removing 8-hydroxyoxycodone from an oxycodone composition containing ~85 ppm of 8-hydroxyoxycodone.

An oxycodone composition containing ~85 ppm of 8-hydroxyoxycodone was subjected to acid catalyzed dehydration in refluxing in toluene with p-toluenesulfonic acid as described in EXAMPLE 24. A sample of the resulting oxycodone product (1.35 g, 4.29 mmol), and EDTA (15 mg) were dissolved in 0.2 N aqueous HCl (27 mL), and the pH raised to 6.1 with 1 M aqueous $Na_2CO_3$ solution. The solution was stirred until the small amount of oxycodone precipitate had dissolved, after which sodium thioglycolate (68.3 mg, 0.60 mmol) was added. After stirring an additional 60 minutes, the pH was raised to 8.1 with 1 M aqueous $Na_2CO_3$ (4.4 mL), and the resulting white precipitate extracted into dichloromethane (3×40 mL). The combined organic extracts were dried over anhydrous sodium sulfate and filtered, and the solvent removed by rotary evaporation to yield an oxycodone product wherein the sum of the 8-hydroxyoxycodone content and the 14-hydroxycodone was less than 5 ppm (see determination in EXAMPLE 26).

EXAMPLE 26

Determination of the Sum of 8-hydroxyoxycodone and 14-hydroxycodeinone Content of the Product of Example 25

A sample of the oxycodone product of EXAMPLE 25 (0.703 g, 2.23 mmol) and p-toluenesulfonic acid monohydrate (0.727 g, 3.8 mmol), and toluene (125 mL) were heated to reflux in a 250 mL round-bottom flask equipped with a reflux condenser. After 2.5 hours, the toluene was removed under reduced pressure at 35-40° C. by rotary evaporation. The resulting residue was dissolved in water (50 mL) and the pH adjusted to 9 by addition of solid sodium carbonate (0.50 g). The aqueous solution was extracted with dichloromethane (3×15 mL), the combined organic layers were dried over anhydrous sodium sulfate and filtered, and the solvent removed under reduced pressure by rotary evaporation. The white solid was further dried under high-vacuum for 15 minutes, and dissolved in 0.1 N aqueous HCl (25 mL). The water was removed under reduced pressure at 30-35° C. by rotary evaporation and the solid dried under high-vacuum to yield oxycodone hydrochloride.

A solution containing 5-mercapto-2-nitro-benzoic acid for use in the analysis of the oxycodone hydrochloride was prepared using the following procedure. In an 8 mL reaction vial, one that accommodates a threaded, Teflon-lined cap and small magnetic stir bar, a pH 7.4 buffer was prepared by dissolving 5 mg of EDTA in 0.1 M aqueous $Na_2HPO_4$ solution (4.75 mL) and 0.1 M aqueous $NaH_2PO_4$ solution (0.25 mL). Dithiothreitol (1.9 mg, 0.012 mmol) was added followed by 5,5'-dithiobis(2-nitro-benzoic acid) (10 mg, 0.025 mmol) which immediately turned the solution color orange. When the solid completely dissolved (5 minutes), the pH of the solution was lowered to 4.6-4.5 with 1 N aqueous HCl solution (0.285 mL). Determination of pH was accomplished using a pH meter with a sufficiently narrow combination electrode (~5 mm) so as to allow its insertion directly into the sample vial.

Figure 11:
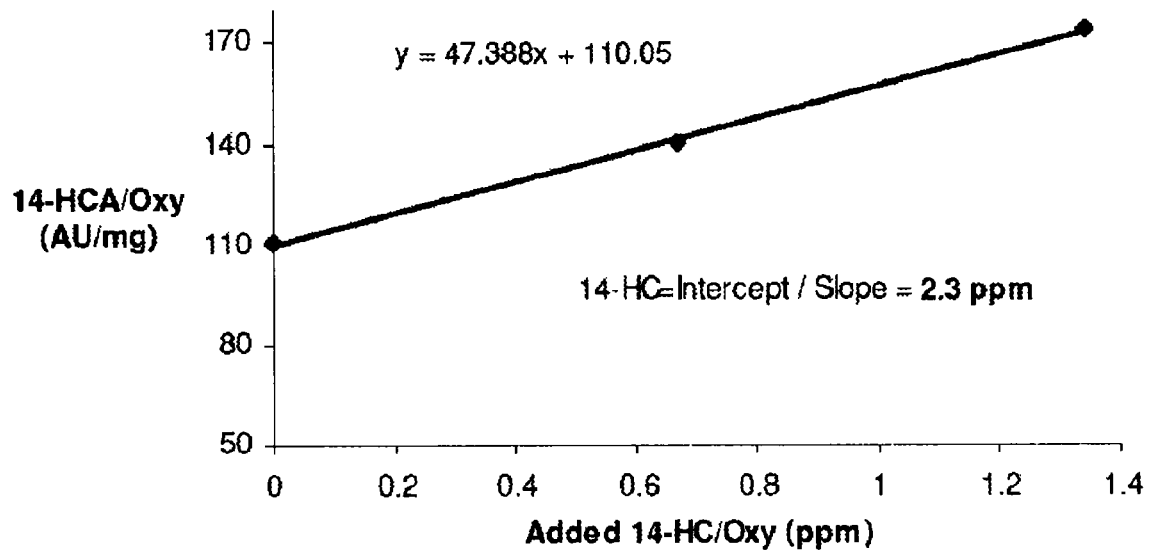

A sample of the oxycodone hydrochloride (579 mg, 1.65 mmol) was placed in an 8 mL reaction vial, to which was added 3.5 ml of the previously prepared solution of 5-mercapto-2-nitro-benzoic acid. The pH of the mixture was raised to 4.5 by addition of 100 mg/mL aqueous $NaH_2PO_4$ solution (0.47 mL), and a 1.0 ml aliquot was removed, diluted with pH 4.5, 0.01 M NaOAc/HOAc buffer solution (10 uL), and stirred. The remainder (2.5 mL) was reserved for separate spike experiments where known amounts of 14-hydroxycodeinone were added to the mixture. After 90 minutes, the pH was lowered to 2 with concentrated HCl (10 uL) and the suspension extracted with ethyl acetate (3×1 mL) by adding the solvent to the vial, capping it, and shaking vigorously. The organic layer was then completely removed from the vial by Pasteur pipet. The aqueous layer was analyzed by HPLC, wherein an analyte in the effluent stream was quantified from its absorbance at 325 nm. The 14-hydroxycodeinone content, and thus the sum of the 8-hydroxyoxycodone content and the 14-hydroxycodeinone content of the product of EXAMPLE 24, was 2.3 ppm as determined from a plot of the area under the 5-(oxycodone-8-sulfanyl)-2-nitro-benzoic acid peak per milligram of oxycodone analyzed versus the amount of 14-hydroxycodeinone added (ppm, i.e. microrams 14-hydroxycodeinone added per gram oxycodone) as shown in FIG. 11.

Plotted on the ordinate is the ratio of the area obtained for the peak corresponding to the thiol-Michael adduct 5-(oxycodone-8-sulfanyl)-2-nitro-benzoic acid (14-HCA) and the weight of oxycodone (Oxy) analyzed, (Area Units (AU)/mg). Plotted on the abscissa is the ratio of the weight of the 14-hydroxycodeinone (14-HC) spike and the weight of oxycodone analyzed, in ppm.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. Any combination of two or more processes, processes steps, or other features of the invention, if not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A process for removing at least one Michael acceptor from a composition, comprising:
treating the composition with a thiol-containing compound under conditions sufficient to remove at least a portion of the at least one Michael acceptor, at least a portion of a thiol-Michael adduct which can form from addition of the thiol-containing compound to the at least one Michael acceptor, or at least a portion of the at least one Michael acceptor and at least a portion of the thiol-Michael adduct, wherein the at least one Michael acceptor is 14-hydroxycodeinone or salt thereof, wherein the thiol-Michael adduct is a thiol-Michael adduct of 14-hydroxycodeinone, wherein the composition comprises oxycodone or acceptable salt thereof.

2. A process for removing at least one Michael acceptor from a composition, comprising:
treating the composition with a suitable soluble thiol-containing compound under conditions sufficient to react with the at least one Michael acceptor, wherein the composition comprises oxycodone or acceptable salt thereof; and
removing from the composition the resulting thiol-Michael adduct, and the unreacted thiol-containing compound, wherein the thiol-containing compound is chosen for its ability to form a soluble thiol-Michael adduct that can be removed from the composition of interest, and, when desirable, quantified, so as to enable determination of the Michael acceptor content of the composition of interest, wherein the at least one Michael acceptor is 14-hydroxycodeinone or salt thereof, wherein the thiol-Michael adduct is a thiol-Michael adduct of 14-hydroxycodeinone.

3. A process of claim 1 wherein the composition is treated with a suitable thiol which has been immobilized on a solid support.

4. A process of claim 1 comprising producing a product, wherein no single Michael acceptor or salt thereof is present in an amount exceeding 25 ppm.

5. A process of claim 1 comprising producing a product, wherein no single Michael acceptor or salt thereof is present in an amount exceeding 10 ppm.

6. A process of claim 1 comprising producing a product, wherein no single Michael acceptor or salt thereof is present in an amount exceeding 5 ppm.

7. A process of claim 1 comprising producing a product, wherein no single thiol-Michael adduct or salt thereof is present in an amount exceeding 25 ppm.

8. A process of claim 1 comprising producing a product containing oxycodone or acceptable salt thereof that contains 14-hydroxycodeinone or salt thereof in an amount of less than 25 ppm.

9. A process of claim 1 comprising producing a product containing oxycodone or acceptable salt thereof that contains 14-hydroxycodeinone or salt thereof in an amount of less than 10 ppm.

10. A process of claim 1 comprising producing a product containing oxycodone or acceptable salt thereof that contains 14-hydroxycodeinone or salt thereof in an amount of less than 5 ppm.

11. A process of claim 1 comprising producing a product containing oxycodone or acceptable salt thereof that contains 14-hydroxycodeinone or salt thereof in an amount of less than 1 ppm.

12. A process of claim 2 comprising quantifying at least one Michael acceptor wherein the amount of thiol-Michael adduct is measured and related to the Michael acceptor content of the composition, and wherein the limit of quantification of the amount of any one Michael acceptor contaminant is 10 ppm or less.

13. A process of claim 2 comprising quantifying the Michael acceptor wherein the amount of thiol-Michael adduct is measured and related to the Michael acceptor content of the composition, and wherein the limit of quantification of the amount of any one Michael acceptor contaminant is in the range of 0.001-10 ppm.

14. A process of claim 2 comprising quantifying the Michael acceptor content of the composition or related alkaloid or acceptable wherein the amount of thiol-Michael adduct is measured and related to the Michael acceptor content of the composition, and wherein the limit of quantification of the amount of the Michael acceptor contaminant is 10 ppm or less.

15. A process of claim 2 comprising quantifying the Michael acceptor content of the composition or related alkaloid or acceptable wherein the amount of thiol-Michael adduct is measured and related to the Michael acceptor content of the composition, and wherein the limit of quantification of the amount of the Michael acceptor contaminant is 1 ppm or less.

16. A process of claim 2 wherein the amount of thiol-Michael adduct is measured and related to the Michael acceptor content of the composition, and wherein the limit of quantification of the level of the Michael acceptor is in the range of 0.001-10 ppm.

17. A process of claim 2 comprising quantifying the 14-hydroxycodeinone content of oxycodone or acceptable salt thereof wherein the amount of thiol-Michael adduct of 14-hydroxycodeinone is measured and related to the 14-hydroxycodeinone content of the composition, and wherein the limit of quantification of the level of the 14-hydroxycodeinone contaminant is 10 ppm or less.

18. A process of claim 2 comprising quantifying the 14-hydroxycodeinone content of oxycodone or acceptable salt thereof wherein the amount of thiol-Michael adduct of 14-hydroxycodeinone is measured and related to the 14-hydroxycodeinone content of the composition, and wherein the limit of quantification of the level of the 14-hydroxycodeinone contaminant is less than 1 ppm.

19. A process of claim 2 comprising quantifying the 14-hydroxycodeinone content of oxycodone or acceptable salt thereof wherein the amount of thiol-Michael adduct of 14-hydroxycodeinone is measured and related to the 14-hydroxycodeinone content of the composition, and wherein the limit of quantification of the level of the 14-hydroxycodeinone contaminant is within the range 0.001-10 ppm.

20. A process of claim 1 wherein the composition comprises an organic base whose solubility in water decreases with increasing pH; and wherein the composition is treated with a suitable thiol-containing compound in aqueous solution at a suitable pH value to form (with the contaminating Michael acceptor) a soluble thiol-Michael adduct; and wherein the organic base is then separated from the thiol-Michael adduct and excess thiol-containing compound by raising the pH to a suitable value so as to precipitate the composition from the solution of soluble thiol-Michael adduct and excess thiol-containing compound.

21. A process of claim 2, wherein the composition is separated from thiol-Michael adduct and excess thiol-containing compound by selective precipitation and/or extraction utilizing water and/or other solvents and/or by selective absorption on media, such as, but not restricted to, ion-exchange resins, and/or other solid supports containing immobilized liganded metal ions, and/or immobilized maleimides, and/or immobilized reactive disulfides, and/or immobilized antibodies and/or immobilized enzymes.

22. A process for removing at least one Michael acceptor, at least one Michael acceptor hydrate, or at least one Michael acceptor and at least one Michael acceptor hydrate from a composition, comprising:

treating the composition with an acidic catalyst under conditions sufficient to remove the at least one Michael acceptor hydrate by converting the at least one Michael acceptor hydrate to a Michael acceptor, wherein the composition comprises oxycodone or acceptable salt thereof; and then treating the composition with a suitable soluble thiol-containing compound under conditions sufficient to remove from the composition the unreacted thiol-containing compound, the at least one Michael acceptor originally present in the composition; and the Michael acceptor formed from the at least one Michael hydrate; and wherein the thiol-containing compound is chosen for its ability to form a soluble thiol-Michael adduct that can be removed from the composition of interest, and, when desirable, quantified, so as to enable determination of the Michael acceptor hydrate content and the Michael acceptor content of the composition of interest, wherein the Michael acceptor hydrate is 8-hydroxyoxycodone or salt thereof.

23. A process of claim 22 comprising producing a product containing oxycodone or acceptable salt thereof that contains 8-hydroxyoxycodone or salt thereof in an amount of less than 100 ppm.

24. A process of claim 22 comprising producing a product containing oxycodone or acceptable salt thereof that contains 8-hydroxyoxycodone or salt thereof in an amount of less than 10 ppm.

25. A process of claim 22 comprising producing a product containing oxycodone or acceptable salt thereof that contains 8-hydroxyoxycodone or salt thereof in an amount of less than 5 ppm.

* * * * *

UNITED STATES PATENT AND TRADEMARK OFFICE
CERTIFICATE OF CORRECTION

| | | |
|---|---|---|
| PATENT NO. | : 7,875,623 B2 | Page 1 of 1 |
| APPLICATION NO. | : 11/603956 | |
| DATED | : January 25, 2011 | |
| INVENTOR(S) | : Jules A. Shafer et al. | |

It is certified that error appears in the above-identified patent and that said Letters Patent is hereby corrected as shown below:

In claim 14 at column 32, lines 11-12, please delete "or related alkaloid or acceptable".

In claim 15 at column 32, lines 18-19, please delete "or related alkaloid or acceptable".

Signed and Sealed this
Seventh Day of June, 2011

David J. Kappos
*Director of the United States Patent and Trademark Office*